United States Patent [19]
Pandey et al.

[11] Patent Number: 5,498,710
[45] Date of Patent: Mar. 12, 1996

[54] ALKYL ETHER ANALOGUES OF BENZOPORPHYRIN DERIVATIVES

[75] Inventors: Ravindra K. Pandey, Williamsville, N.Y.; Thomas J. Dougherty, Grand Island, both of N.Y.; Kevin M. Smith, Davis, Calif.; Isabelle Meunier, Tournus, France

[73] Assignees: Health Research, Inc., Buffalo, N.Y.; The Regents of the University of California, Oakland, Calif.

[21] Appl. No.: 231,113

[22] Filed: Apr. 22, 1994

[51] Int. Cl.⁶ .................................................. C07D 487/22
[52] U.S. Cl. .................................................. 540/145
[58] Field of Search ...................................... 540/145

[56]         References Cited
         U.S. PATENT DOCUMENTS

| | | | |
|---|---|---|---|
| 4,996,312 | 2/1991 | Sakata et al. | 540/145 |
| 5,093,349 | 3/1992 | Pandey et al. | 540/145 |
| 5,149,708 | 9/1992 | Dolphin et al. | 514/410 |

OTHER PUBLICATIONS

Pandey et al. J. Chem. Soc. Perkin Trans. pp. 1377–1385; 1992.
Pandey, R. et al., "Efficient Syntheses of New Classes of Regio-Chemically Pure Benzoporphyrin Derivatives", Bioorganic & Medicinal Chemistry Letters, vol. 3, No. 12, pp. 2615–2618 (1993).
Dougherty, T. et al., "Photodynamic Therapy for the Treatment of Cancer: Current Status and Advances", Photodynamic Therapy of Neoplastic Diseases, pp./ 1–19, CRC Press, Boca Raton FL.
Pandey, R. et al, "Chemistry of Photofrin II and Some New Photosensitizers", SPIE vol. 1065 Photodynamic Therapy: Mechanisms (1989) pp. 164–174.
Richter, A. et al., "Preliminary Studies on a More Effective Phototoxic Agent Than Hematoporphyrin", JNCI, vol. 79, No. 6, Dec. 1987, pp. 1327–1332.
Pandey, R. et al., "Chlorin and Porphyrin Derivatives as Potential Photosensitizers in Photodynamic Therapy," Photochemistry and Photobiology, vol. 53, No. 1, pp. 65–72, (1991).
Meunier, I. et al., "New Syntheses of Benzoporphyrin Derivatives and Analogues for Use in Photodynamic Therapy," Biorganic & Med. Chemistry Letters, vol. 2, No. 12, pp. 1575–1580 (1992).
Morgan, A. et al., "Ready Syntheses of Benzoporphyrins via Diels–Alder Reactions with Protoporphyrin IX", J. Chem. Soc., Chem. Commun., 1984 pp. 1047–1048.
Pandey, R. et al., "Long Wavelength Photosensitizers Related to Chlorins and Bacteriochlorins for use in Photodynamic Therapy", J. Chem. Soc. Perkin Trans. 1 (1992) pp. 1377–1385.
Pandey, R. et al., "Porphyrin Dimers as Photosensitizers in Photodynamic Therapy", J. Med. Chem. (1990) 33, pp. 2032–2038.
Pandey, R. et al., "Efficient Synthesis of Porphyrin Dimers with Carbon—Carbon Linkages", Tetrahedron Letters, vol. 31, No. 6, pp. 789–792 (1990).
Pandey, R. et al., "Syntheses of Porphyrin and Chlorin Dimers for Photodynamic Therapy", SPIE vol. 1426 Optical Methods for Tumor Treatment and Early Diagnosis: Mechanisms and Techniques (1991) pp. 356–361.

*Primary Examiner*—Mukund J. Shah
*Assistant Examiner*—Pavanaram K. Sripada
*Attorney, Agent, or Firm*—Michael L. Dunn

[57]         ABSTRACT

Compounds having properties superior to known photosensitizers defined by the following chemical formula:

including R groups $R^1$, $R^2$, $R^3$, and $R^4$, wherein $R^1$ and $R^2$ are methyl or —CH(O—$(CH_2)_n CH_3$)$CH_3$ or are joined together to form the group D and wherein $R^3$ and $R^4$ are methyl or —CH(O—$(CH_2)_n CH_3$)$CH_3$ or are joined together to form the group D; provided that one of $R^1$ and $R^2$ or $R^3$ and $R^4$ are joined together to form the group D wherein one of the remaining R groups is methyl and one of the remaining R groups is —CH(O—$(CH_2)_n CH_3$)$CH_3$, where n is an integer of 5 through 7 and group D is:

and $R_5$ is independently at each occurrence —$OR_6$ where $R_6$ is lower alkyl of 1 through 7 carbon atoms or $R_6$ is an amino acid residue.

4 Claims, 8 Drawing Sheets

FIGURE 4

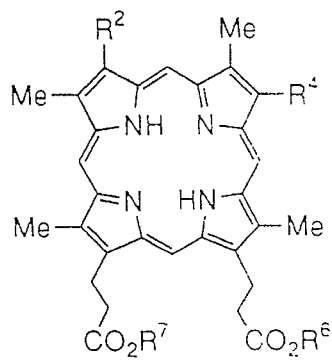

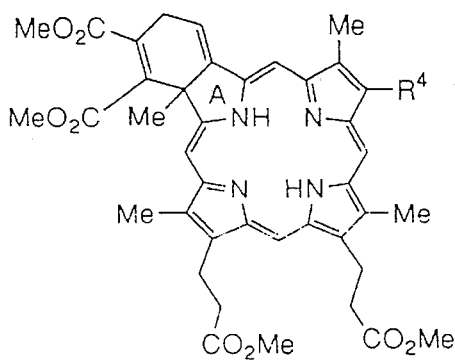

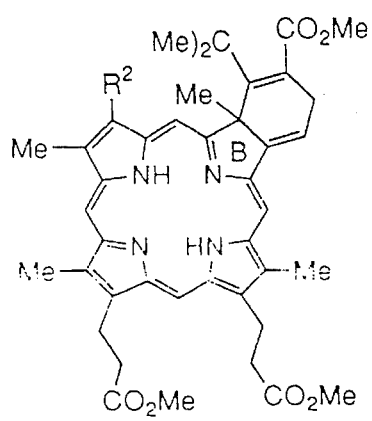

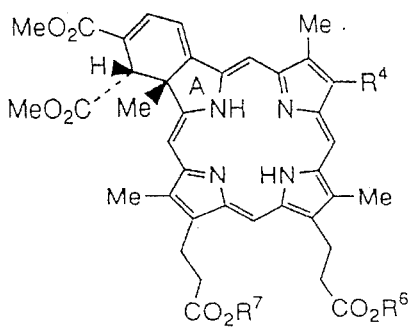

20 $R^4$ = CH=CH$_2$; $R^6$ = $R^7$ = Me
21 $R^4$ = CH=CH$_2$; $R^6$ = H; $R^7$ = Me
22 $R^4$ = CH=CH$_2$; $R^6$ = Me; $R^7$ = H
23 $R^4$ = CO.Me; $R^6$ = $R^7$ = Me
24 $R^4$ = CH(OH)Me; $R^6$ = $R^7$ = Me
25 $R^4$ = Et; $R^6$ = $R^7$ = Me
26 $R^4$ = CHO; $R^6$ = $R^7$ = Me
27 $R^4$ = CH(O-hexyl)Me; $R^6$ = $R^7$ = Me

FIGURE 8

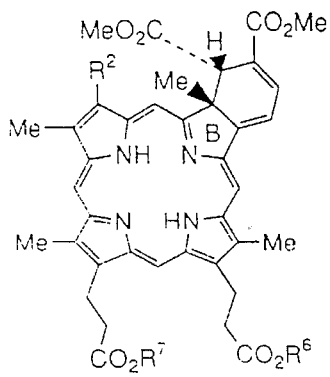

28 $R^2$ = CH=CH$_2$; $R^6$ = $R^7$ = Me
29 $R^2$ = CH=CH$_2$; $R^6$ = H; $R^7$ = Me
30 $R^2$ = CH=CH$_2$; $R^6$ = Me; $R^7$ = H
31 $R^2$ = CO.Me; $R^6$ = $R^7$ = Me
32 $R^2$ = CH(OH)Me; $R^6$ = $R^7$ = Me
33 $R^2$ = Et; $R^6$ = $R^7$ = Me
34 $R^2$ = CHO; $R^6$ = $R^7$ = Me
35 $R^2$ = CH(O-hexyl)Me; $R^6$ = $R^7$ = Me

FIGURE 9

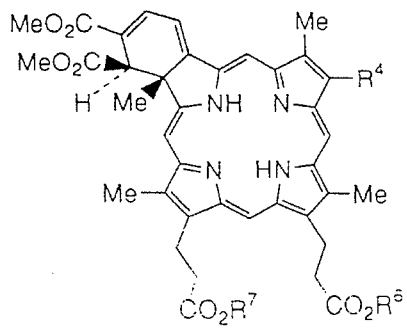

36 $R^4$ = CH=CH$_2$; $R^6$ = $R^7$ = Me
37 $R^4$ = CO.Me; $R^6$ = $R^7$ = Me
38 $R^4$ = CH(OH)Me; $R^6$ = $R^7$ = Me
39 $R^4$ = Et; $R^6$ = $R^7$ = Me
40 $R^4$ = CH(O-hexyl)Me; $R^6$ = $R^7$ = Me

FIGURE 10

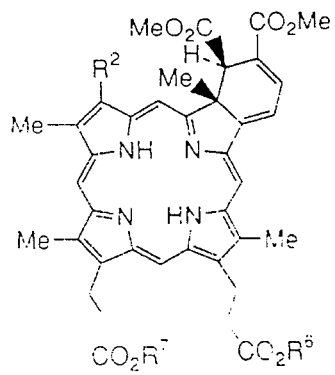

41 $R^2$ = CH=CH$_2$; $R^6$ = $R^7$ = Me
42 $R^2$ = CO.Me; $R^6$ = $R^7$ = Me
43 $R^2$ = CH(OH)Me; $R^6$ = $R^7$ = Me
44 $R^2$ = Et; $R^6$ = $R^7$ = Me
45 $R^2$ = CH(O-hexyl)Me; $R^6$ = $R^7$ = Me FIGURE 11
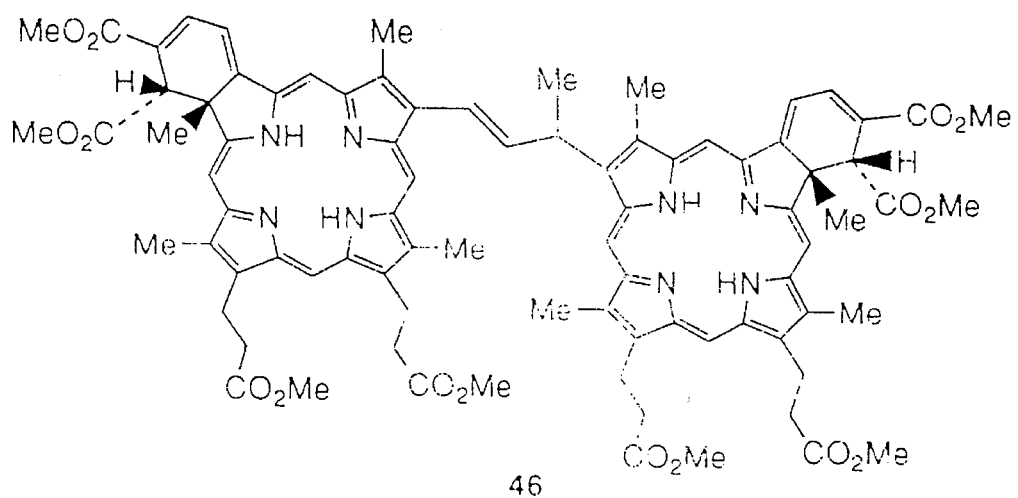
46
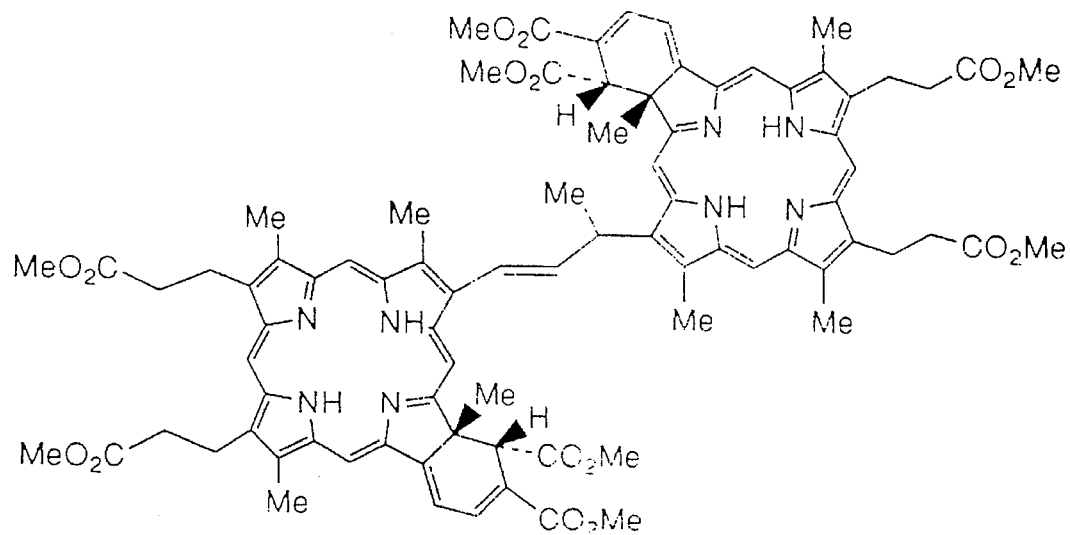
47
FIGURE 12

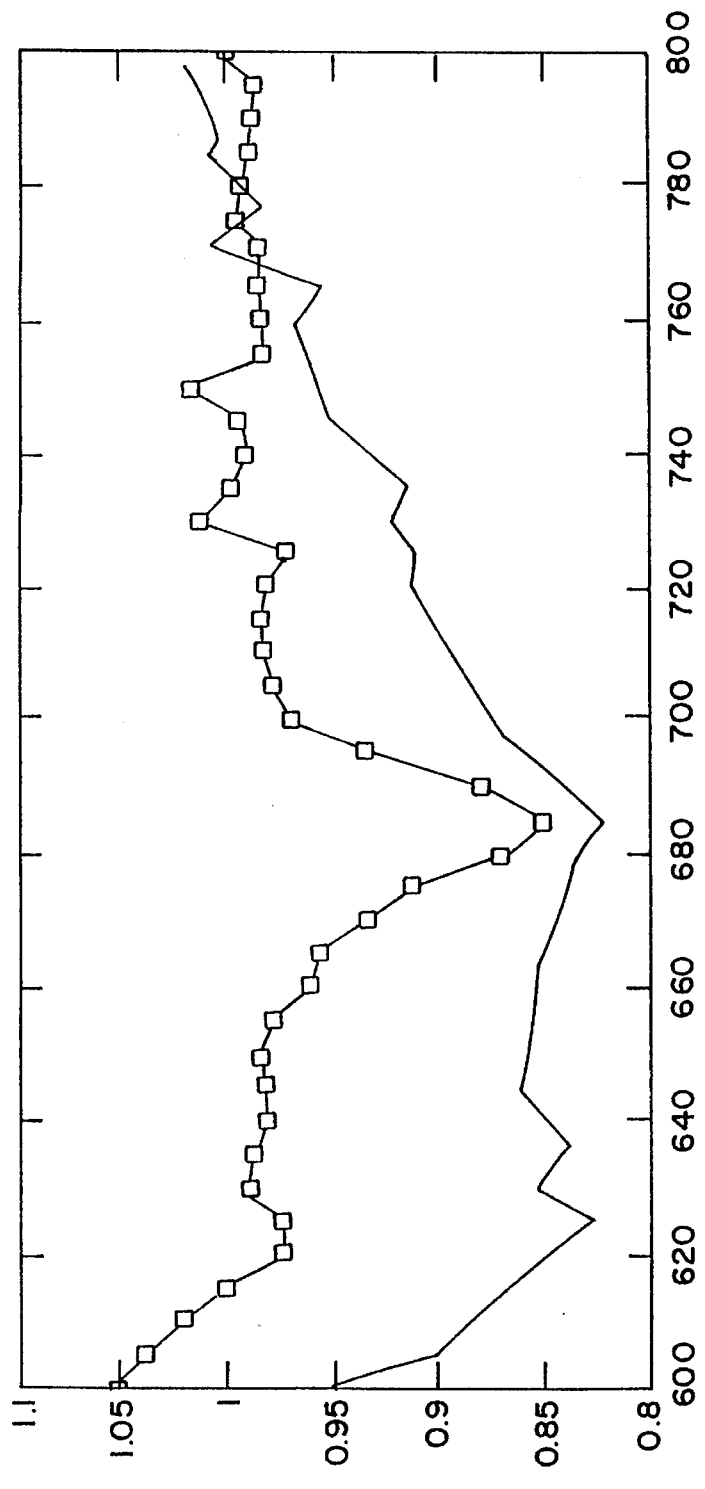

ALKYL ETHER ANALOGUES OF BENZOPORPHYRIN DERIVATIVES

This work was supported by grants from the National Institutes of Health (CA 55791, HL 22252). The United States Government may have certain rights in the invention.

BACKGROUND OF THE INVENTION

In order to obtain maximum tissue penetration, long wavelength absorbing photosensitizers have generated a great deal of interest as potential candidates for photodynamic therapy (PDT) (Dougherty, T. J. [1990] "Photodynamic Therapy For the Treatment of Cancer: Current Status and Advances", *Photodynamic Therapy of Neoplastic Disease*, pp. 1–20, CRC Press, Boca Raton, Fla.). Among such photosensitizers, a chlorin type benzoporphyrin derivative (BPD), a mixture of 21 and 22 as shown in FIG. 7, has been reported as a promising second generation photosensitizer for the treatment of cancer (Pandey, R. K.; Majchrzycki, D. F.; Dougherty, T. J.; and Smith, K. M., [1989] "Chemistry of Photofrin II and Some New Photosensitizers", *Proc. SPIE*, 1065, pp. 164–174). BPD is obtained as a mixture of isomers (ring "A" and ring "B" modified) by first reacting protoporphyrin IX dimethyl ester with dimethyl acetylenedicarboxylate; the Diels Alder adduct so obtained is then rearranged to the double-bond conjugated compound by treatment with 1,8-diaza bicyclo [5,4,0] undec 7 ene (DBU). The partially hydrolyzed monomethyl ester (as a mixture) of the ring "A" benzoporphyrin is claimed to be the most promising second generation PDT agent, and is currently in Phase I clinical trials (Richter, A. M.; Kelly, B.; Chow, J.; Liu, J. D.; Towers, G. H. N.; Levy, J.; and Dolphin, D., [1987] "Preliminary Studies on a More Effective phototoxic Agent Than Hematoporphyrin", *J. Natl. Cancer Inst.*, 79, pp. 1327–1332).

Because photosensitizers for PDT are still not as effective as desired, there has been continuing effort to prepare more effective photosensitizers. Examples of such efforts are, for example, described in (a) Pandey, R. K.; Bellnier, D. A.; Smith, K. M.; Dougherty T. J. [1991] "Chlorin and Porphyrin Derivatives as potential photosensitizers in photodynamic Therapy", *Photochem. Photobiol.*, 53, 65–72; (b) Bellnier, D. A.; Henderson, B. W.; Pandey, R. K.; Potter, W. R.; Dougherty, T. J., [1993] "Murine Pharmacokinetics and Antitumor Efficacy of the Photodynamic Sensitizer 2-(1-hexyloxyethyl)-2-devinylpyropheophorbide-a (HPPH), *J. Photochem. Photobiol.*, 20, 55–61; (c) Pandy, R. K.; Shiau, F.-Y.; Sumlin, A. B.; Dougherty, T. J.; Smith, K. M., [1992] "Structure/Activity Relationships Among Photo-Sensitizers Related to Pheophorbides and Bacteriopheophorbides", *Bioorg. Med. Chem. Lett.*, 2, 491–496; (d) Meunier, I.; Pandey, R. K. p Walker, M. M.; Senge, M. O.; Dougherty, T. J.; Smith, K. M., [1992] "New Syntheses of Benzoporphyrin Derivatives and Analogues for Use in Photodynamic Therapy", *Bioorg. Med. Chem. Lett.*, 2, 1575–1580; and (e) Evenson, J. F.; Sommer, S.; Rimington, C.; Moan, J., 1987] "Photodynamic Therapy of CH3 Mouse Mammary Carcinoma with Hematoporphyrin Diethers as Sensitizers", *Br. J. Cancer*, 55, 483–486.

Recently, an alternate route for the preparation of BPDs has been reported and showed that treatment of the initial unconjugated Diels Alder adduct with triethylamine gives the trans isomer, which upon subsequent treatment with DBU produces the cis isomer (red shifted by 6 nm) in modest yield (Meunier, I.; Pandey, R. K.; Walker, M. M.; Senge, M. O.; Dougherty, T. J.; and Smith, K. M., [1992] "New Syntheses of Benzoporphyrin Derivatives and Analogues for Use in Photodynamic Therapy", *Bioorg. Med Chem. Lett.*, 2, pp. 1575–1580). The cis- isomer, as a mixture of 20 and 28,can also be obtained by reacting the initial unconjugated Diels Alder adduct from protoporphyrin IX dimethyl ester 3 directly with DBU. Among BPDs tested so far, the biological activity of only the cis- isomers [ring "A" modified, (21, 22)] and [ring "B" modified, (29, 30 shown in FIG. 8)] of BPD (as a mixture of two monomethyl esters) have been reported. Richter et al. supra have shown that the BPD in which ring "A" is modified is more active than ring "B" modified isomer.

BRIEF DESCRIPTION OF THE DRAWINGS

FIG. 1A shows ring "B" modified compound 35. FIG. 1B shows ring "A" modified compound 27. FIG. 1C shows ring "B" modified compound 45 and FIG. 1D shows ring "A" modified compound 40.

FIG. 4 illustrates the structural formulas for compounds 1–13.

FIG. 5 illustrates the structural formulas for compounds 14–16.

FIG. 6 illustrates the structural formulas for compounds 17–19.

FIG. 7 illustrates the structural formulas for compounds 20–27.

FIG. 8 illustrates the structural formulas for compounds 28–35.

FIG. 9 illustrates the structural formulas for compounds 36–40.

FIG. 10 illustrates the structural formulas for compounds 41–45.

FIG. 11 illustrates the structural formula for compound 46.

FIG. 12 illustrates the structural formula for compound 47.

FIG. 14 shows an in vivo absorption spectrum of compound 13.

BRIEF DESCRIPTION OF THE INVENTION

Figure 1A:
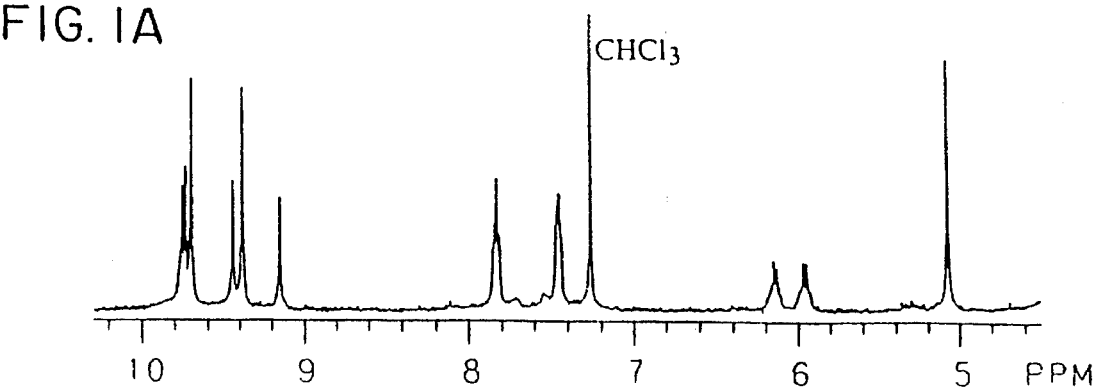
FIGS. 1A–1D show the $^1$HNMR spectrum $\delta 4.5$–10.5 region in $CDCl_3$, of hexyl ether BPDs.
Figure 1B:
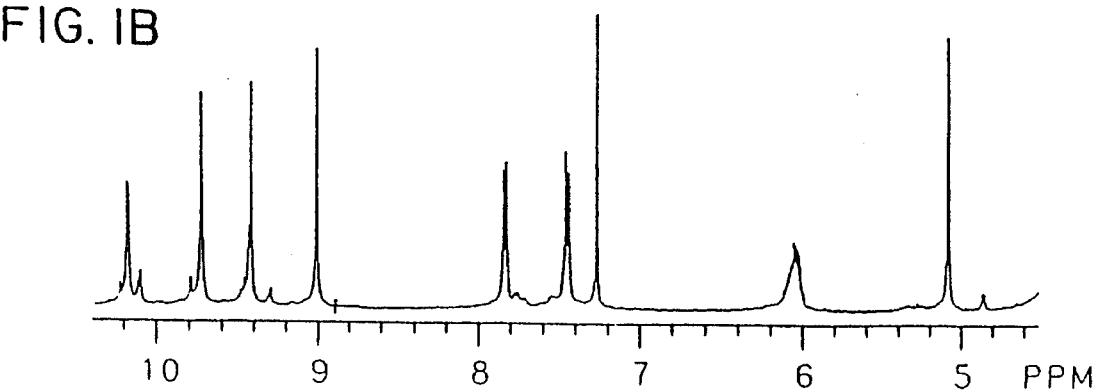

In accordance with the present invention there are provided new benzoporphyrin derivatives having utility as fluorescent and photosensitizing compounds. Such compounds may be excited by microwaves, ultrasound, and visible or infrared radiation.

All of such novel compounds described herein may be used in traditional areas where compounds having such properties have utility. The compounds may, for example, be incorporated into a substance such as a plastic product, excited with ultrasound, microwaves or visible light followed by using known methods for detecting emitted radiation to image the product for the purpose of detecting voids or other flaws in the product.

Certain of such compounds have special utility as photosensitizers in the area of photodynamic therapy for the detection and treatment of tumors.

In accordance with the invention, a series of isomerically pure benzoporphyrin derivatives (cis- and trans- isomers) as methyl esters is described. In in vivo studies, the n-hexyl ether analogues of both cis- and trans- isomers of benzoporphyrin derivatives, i.e., compound 27 in FIG. 7, compound 35 in FIG. 8, compound 40 in FIG. 9, and compound 45 in FIG. 10, were found to be significantly more active than the industrially prepared benzoporphyrin derivative ("BPD" a mixture of 21 and 22 in FIG. 7). Introduction of electron-withdrawing groups onto the macrocyclic nucleus (as in compounds 23, 31, 37 and 42) induced a significant red shift in the absorption spectra, but failed to improve their photosensitizing efficacy. Further studies with photosensitizer 40 showed that, like BPD, it had reduced residual skin phototoxicity compared with Photofrin®. The uptake and clearance characteristics, as well as binding or metabolic shifts of BPD were also compared with the 4-(1-hexyloxy-ethyl-derivative 40 by in vivo reflection spectroscopy.

Such compounds having properties superior to known photosensitizers for such use may be defined by the following chemical formula:

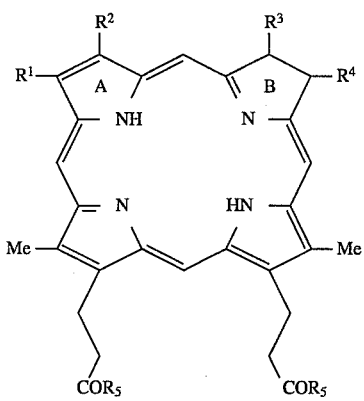

including R groups $R^1$, $R^2$, $R^3$, and $R^4$, wherein $R^1$ and $R^2$ are methyl or —CH(O—$(CH_2)_n$$CH_3$)$CH_3$ or are joined together to form the group D and wherein $R^3$ and $R^4$ are methyl or —CH(O—$(CH_2)_n$$CH_3$)$CH_3$ or are joined together to form the group D; provided that one of $R^1$ and $R^2$ or $R^3$ and $R^3$ are joined together to form the group D wherein one of the remaining R groups is methyl and one of the remaining R groups is —CH(O—$(CH_2)_n$$CH_3$)$CH_3$, where n is an integer of 5 through 7 and group D is:

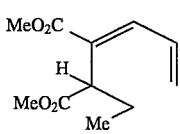

and $R_5$ is independently at each occurrence —$OR_6$ where $R_6$ is lower alkyl of 1 through 7 carbon atoms or $R_6$ is an amino acid residue.

A preferred amino acid residue is the residue of aspartic acid (i.e.,

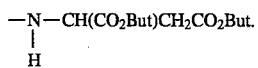

Further particular compounds having such improved properties may be represented by the formulas:

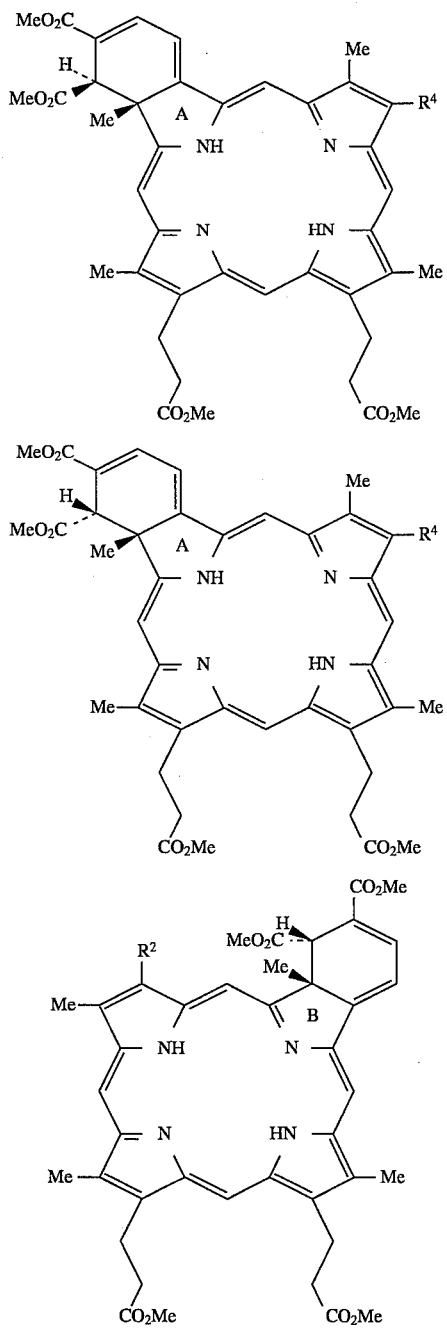

DETAILED DESCRIPTION OF THE INVENTION

In our efforts to understand the structure/activity relationships in this intriguing class of compounds, a series of BPDs (methyl esters as cis- as well as trans- isomers) were synthesized and evaluated for their photosensitizing efficacy vis-a-vis commercial BPD.

In this study, chlorins were initially used such as pheophorbide-a and methyl pheophorbide-a as substrates, and a series of alkyl ether analogues were prepared with variable ether carbon lengths using procedures generally described in Pandey, R. K.; Bellnier, D. A.; Smith, K. M.; Dougherty, T. J., [1991] "Chlorin and Porphyrin Derivatives as Potential Photosensitizers in Photodynamic Therapy",

*Photochem. Photobiol.*, 53, 65–72; and Bellnier, D. A.; Henderson, B. W.; Pandey, R. K.; Potter, W. R.; Dougherty, T. J., [1993] "Murine Pharmacokinetics and Antitumor Efficacy of the Photodynamic Sensitizer 2-(1-hexyloxyethyl)-2-devinylpyropheophorbide-a (HPPH), *J. Photochem. Photobiol.*, 20, 55–61; Among such derivatives, the hexyl and heptyl ethers were found to be extremely effective, but further increases in the length of the ether carbon chain caused reduction in the in vivo activity. It has also been observed that introduction of electron-withdrawing substituents onto the porphyrin and chlorin skeleton induced sometimes remarkable red shifts in the electronic absorption spectra; moreover, some of these compounds showed significant differences in their photosensitizing activity after introduction of the electronegative functionality (Pandey, R. K.; Shiau, F. -Y.; Sumlin, A. B.; Dougherty, T. J.; Smith, K. M., [1992] "Structure/Activity Relationships Among Photo-Sensitizers Related to Pheophorbides and Bacteriopheophorbides", *Bioorg. Med. Chem. Lett.*, 2, pp. 491–496). In general, replacement of carbonyl with thiocarbonyl groups in chlorin and bacteriochlorin systems not only increased the tumorcidal activity, but also gave a favorable red shift in the absorption spectrum of as much as 30 to 35 nm.

All chemicals used were analytical grade. BPD was a gift from Quadralogic Technologies, Vancouver, Canada. As shown in FIG. 4, the industrial preparation of BPD consists of a mixture of two monomethyl esters 21 and 22, obtained by partial hydrolysis of BPD dimethyl ester 20. BPDs 20 and 28 were obtained, as a mixture, by reacting protoporphyrin IX dimethyl ester with dimethyl acetylenedicarboxylate followed by treatment with DBU. In order to resolve the isomeric problem associated with BPD, we have reported an alternate method in which 4-acetyl-2-vinyldeuteroporphyrin IX dimethyl ester 6 (for ring "A" BPD adduct), and 2-acetyl-4-vinyldeuteroporphyrin IX dimethyl ester 7 (for ring "B" BPD adduct) were used as starting materials. Porphyrins 6 and 7 were then individually converted into a series of BPDs 20–45 (see FIGS. 7–10). The BPDs with acetyl groups were found, as expected, to have longer wavelength absorption maxima than the corresponding vinyl analogues. The unique structures of both the isomers 20 and 36 were confirmed by single X-ray crystal studies. For the preparation of the n-hexyl ether derivatives 27, 40, 35 and 45, the corresponding cis- and trans- isomers of both ring "A" and "B" modified BPDs 20, 36, 28 and 41 were first reacted with 30% HBr in acetic acid, and then with n-hexanol (following standard methodology) and the desired derivatives were obtained each as a mixture of diastereoisomers, in 50 to 55% yields. Proton NMR studies of these compounds provided an independent verification of the precise (ring "A" or ring "B" modified) isomer involved. Besides proton NMR, all the new compounds were also characterized by elemental analysis and/or high resolution mass spectrometry.

Starting from hematoporphyrin-IX dimethyl ester 1, a series of isomerically pure benzoporphyrin derivatives (BPDs) 20, 23–25, 27, 28, 31–33, 35–37, 39, 40, 42, 44 and 45 were synthesized. The bis-porphyrins 46 and 47 with carbon-carbon linkages also were prepared by reacting 3- and 8-(1-hydroxyethyl)-benzoporphyrin derivatives 24 and 32 with triflic acid. In preliminary in vivo studies, the hexyl ether derivatives 27, 35, 40 and 45 (as diastereoisomeric mixtures) appear to have better photosensitizing efficacy than benzoporphyrin derivative monocarboxylic acid (BPD-MA; mixture of 21 and 22). Under similar doses and treatment conditions, other BPDs 23, 25, 26, 31, 33 and 34, along with bis-porphyrins 46 and 47 did not show any significant tumorcidal activity. The structures of the ring "A" modified BPD isomers 20 (cis) and 36 (trans) were confirmed by single crystal X-ray studies. Benzoporphyrin derivative mono-carboxylic acid (BPD-MA) is currently one of the more promising photosensitizers for photodynamic therapy (PDT) (Pandey, R. K.; Majchrzycki, D. F.; Dougherty, T. J.; and Smith, K. M., *Proc. SPIE*, 1989, 1065, p. 164). It is prepared by first reacting protoporphyrin-IX dimethyl ester 3 with dimethyl acetylenedicarboxylate (DMAD) ([a] Callot, H. L.; Johnson, A. W.; Sweeney, A, *J. Chem. Soc. Perkin Trans.* 1, 1973, p. 1424; [b] Morgan, A. R.; Pangka, V. S.; Dolphin, D., *J. Chem. Soc. Chem. Commun.*, 1984, 1047; [c] Pandey, R. K.; Shiau, F. -Y.; Ramachandran, K.; Dougherty, T. J.; Smith, K. M., *J. Chem. Soc., Perkin Trans.* 1, 1992, p. 1377 ). The Diels Alder adduct (obtained as a mixture) is then rearranged to a mixture of ring "A" and ring "B" reduced isomers 20 and 28 respectively. The isomeric mixture is then separated into individual isomers by column chromatography. Partial hydrolysis of the methyl ester derivatives 20 and 28 mainly gave 21, 22 from 20, and 29, 30 from 28. Among these isomers the monomethyl ester derivatives as a mixture of 21 and 22 (the so called BPD-MA) has been reported to be more effective than the ring "B" reduced isomers 29 and 30 (Richter, A. M.; Kelly, B.; Chow, J.; Liu, J. D.; Towers, G. H. N.; Levy, J.; Dolphin, D., *J. Natl. Cancer Inst.*, 1990, 52, p. 501). BPD-MA has a strong absorption peak at 700 nm which potentially should allow deeper tissue penetration and greater activation than Photofrin®. Earlier studies in animal tumor models have also confirmed that BPD-MA is an effective photosensitizer if the animals are treated 3 h post intravenous (i.v.) injection of the drug (Richter, A. M.; Waterfield, E.; Jain, A. K.; Allison, B., *Br. J. Cancer*, 1991, 63, p. 87). At similar or higher does, no tumor response was observed if the treatment was done 24 h post i.v. injection. In order to understand the structure activity relationships among BPDs, and also to avoid the tedious separation of the various isomers in the last steps of the synthesis, we have developed an efficient alternate approach for the synthesis of such analogues.

In our synthetic approach, hematoporphyrin-IX dimethyl ester 1, obtained by the reaction of commercially available hematoporphyrin-IX dicarboxylic acid 2 with diazomethane was used as the starting material. Partial oxidation of 1 with tetrapropylammonium perruthenate/N-methylmorpholine N-oxide gave a mixture of mono-acetyl-mono-(1-hydroxyethyl)porphyrins which were efficiently separated into individual isomers 4 and 5 by preparative HPLC in gram quantities ([a] Pandey, R. K.; Smith, K. M; Dougherty, T. J., *J. Med. Chem.*, 1990, 33, p. 2032; and [b] Shiau, F. -Y.; Pandey, R. K.; Ramaprasad, S.; Dougherty, T. J.; Smith, K. M., *J. Org. Chem.*, 1990, 55, p. 2190). HPLC conditions: (Preparative) Waters Associates Prep LC3000 system attached to a Waters 1000 PrepPak module with PrepPak-500 silica gel cartridge; Solvent, 2.5% THF in $CH_2Cl_2$; 50.0 $cm^3$/min; Waters 484 tunable absorbance detector set at 405 nm. (Analytical) Waters Associates 510 pump, 600E solvent delivery system; Waters Porasil 10µ stainless steel column (30 cm×3.9 mm i.d.); Solvent, 3% THF in $CH_2Cl_2$; 3.5 $cm^3$/min; Waters 490E programmable multiwavelength detector set at 405 nm; Retention times: 4, 16 min; 5, 19 min. The mono-(1-hydroxyethyl)phorphyrins were then individually converted into the corresponding mono-acetyl-mono-vinyl-(6 and 7) and mono-ethyl-mono-vinyl analogues 12 and 13 in a number of steps by following the literature procedure (Pandey, R. K.; Smith, K. M; Dougherty, T. J., *J. Med. Chem.*, 1990, 33, p. 2032). In brief, for the preparation of 8-acetyl-3-vinyldeuteroporphyrin-IX dimethyl ester 6 (IUPAC nomenclature), 8-acetyl-3-(1-hydroxyethyl)deuteroporphyrin-IX dimethyl ester 4 was refluxed with o-dichlorobenzene in presence of p-toluene sulphonic acid to afford 8-acetyl-3-vinyldeuteroporphyrin-IX dimethyl ester 6 in 90% yield. 3-Acetyl-8-vinyldeuteroporphyrin-IX dimethyl ester 7 was prepared from porphyrin 5 by following the methodology as discussed for the preparation of 6. For the synthesis of 3-ethyl-8-vinyldeuteroporphyrin dimethyl ester 12, the zinc(II) complex of 8-acetyl-3-vinyldeuteroporphyrin-IX dimethyl ester 6 was hydrogenated over Pd—C to give the corresponding 3-ethylporphyrin (Zn complex) in quantitative yield. Removal of zinc was easily achieved by briefly treating with trifluoroacetic acid. The acetylporphyrin 8 was then converted into 3-ethyl-8-vinyldeuteroporphyrin-IX dimethyl ester 12 by the method discussed above. Along similar lines, starting from 3-acetyl-8-vinyl deuteroporphyrin 7,8-ethyl-3-vinylporphyrin 13 was also prepared in 56% over all yield.

For the preparation of the ring "A" modified 8-acetylbenzoporphyrin derivatives 23 and 37, 8-acetyl-3-vinyldeuteroporphyrin-IX dimethyl ester 6 was reacted with DMAD, using toluene as a solvent. The reaction was monitored by spectrophotometry, and the "intermediate" Diels-Alder adduct 15 so obtained was isolated pure in 50% yield. Treatment of the intermediate adduct with DBU, following the literature (Morgan, A. R.; Pangka, V. S.; Dolphin, D., *J. Chem. Soc. Chem. Commun.*, 1984, p. 1047), gave the rearranged cis isomer 23 in 45% yield after tedious chromatographic separation. However, when the intermediate adduct was rearranged with triethylamine, the trans isomer was isolated in 50% yield after simple column chromatography. The trans isomer 37, upon further treatment with DBU, conveniently gave the cis isomer 23 in almost quantitative yield (Meunier, I.; Pandey, R. K.; Walker, M. M.; Senge, M. O.; Dougherty, T. J.; Smith, K. M., *Bioorg. Med. Chem. Lett.*, 1992, 2, p. 1575). In order to prepare a series of vinyl-BPDs 20, 28, 36 and 41 (i.e. cis- and trans- isomers) the acetyl derivatives 23, 31, 37 and 42 were first reduced to the corresponding (1-hydroxyethyl) analogues 24, 32, 38 and 43, respectively, and then refluxed with o-dichlorobenzene containing a catalytic amount of p-toluene sulphonic acid. The desired vinyl-BPDs were obtained in excellent yields. The 3-ethyl- and 8-ethylbenzoporphyrin derivatives 25, 33, 39 and 44 were obtained by reacting the vinylporphyrins 12 and 13 with DMAD and then treating them consecutively with triethylamine and DBU. In the pyropheophorbide series, we had already observed (Pandey, R. K.; Shiau, F. -Y.; Sumlin, A. B.; Dougherty, T. J.; Smith, K. M., *Bioorg. Med. Chem. Lett.*, 1992, 2, p. 491) that replacement of the vinyl group at position 3 with a formyl substituent made a significant difference in biological activity. In order to investigate the effect of such a formyl substituent in the BPD series, 3-vinyl-and 8-vinyl-BPDs 20 and 28 were first reacted with sodium periodate and osmium tetroxide (catalytic amount) (Pandey, R. K.; Shiau, F.-Y.; Sumlin, A. B.; Dougherty, T. J.; Smith, K. M., *Bioorg. Med. Chem. Lett.*, 1992, 2, p. 491) to give the resulting formyl-BPDs 26 and 34 in >80% yields. Like acetyl-BPDs, the formyl derivatives also have a strong absorption in the red at 696 nm.

In porphyrins, chlorins, pheophorbides, pyropheophorbides and purpurin series of pigments it has been observed that conversation of the vinyl group(s) into alkyl ether side chain(s), always increases the efficacy of the parent vinyl-pigment ([a] Pandey, R. K.; Shiau, F. -Y.; Sumlin, A. B.; Dougherty, T. J.; Smith, K. M., *Bioorg. Med. Chem. Lett.,* 1992, 2, p. 491; [b1] Pandey, R. K., Bellnier, D. A.; Smith, K. M.; Dougherty, T. J.; *Photochem. Photobiol,* 1991, 53, 65; [b2] Bellnier, D. A.; Henderson, B. W.; Pandey, R. K.; Potter, W. R.; Dougherty, T. J., *J. Photochem. Photobiol. Part B: Biol.* 1993, 20,p. 55; [c] Evenson, J. F.; Sommer, S.; Rimington, C.; Moan, J., *Br. J. Cancer,* 1987, 55, p. 483). Among such alkyl ether derivatives, it has been observed that biological activity increases with the length of carbon chain, with n-hexyl and n-heptyl being the most effective; further increasing the length of carbon chain resulted in a significant decrease in biological activity. In order to establish a generic requirement for an effective photosensitizer, we prepared the hexyl ether derivatives of the cis- and trans isomers of both ring "A" and ring "B" modified benzoporphyrin derivatives, and these were compared with the biological activity of the corresponding vinyl-analogues 20, 28, 36 and 41, respectively. For the preparation of the hexyl ether derivatives, 27 and 35, (the cis isomers of ring "A" and ring "B" modified BPDs), the 3- and 8-vinylbenzoporphyrin derivatives 20 and 28 were separately treated with 30% HBr/acetic acid; the intermediate (1-bromoethyl) derivatives were not isolated but were immediately reacted with n-hexanol under a nitrogen atmosphere. The respective (1-hexyloxyethyl) derivative 27 or 35 were obtained in approximately 50% yield. BPD derivatives 40 and 45 (trans isomer) were obtained from the corresponding (1-hydroxyethyl) derivatives 38 and 43,which in turn were obtained from the corresponding acetyl analogues 37 and 42, and also from related vinyl analogues 36 and 41.

Figure 1C:
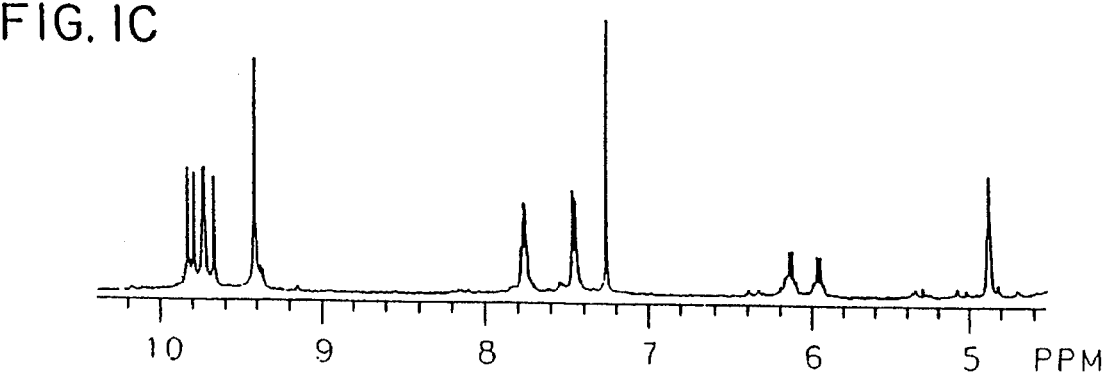
Figure 1D:
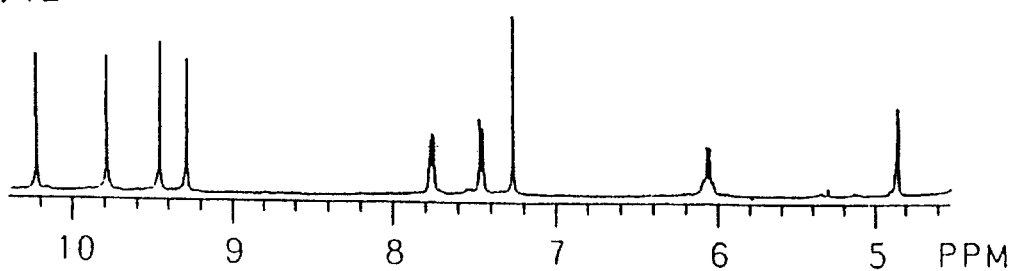

For the syntheses of benzoporphyrin derivatives with variable substituents, 3- and 8- vinyl-BPDs were initially prepared by following the literature method ([a] Callot, H. L.; Johnson, A. W.; Sweeney, A, *J. Chem. Soc. Perkin Trans.* 1, 1973, p. 1424; [b] Morgan, A. R.; Pangka, V. S.; Dolphin, D., *J. Chem. Soc. Chem. Commun.,* 1984, 1047; [c] Pandey, R. K.; Shiau, F. -Y.; Ramachandran, K.; Dougherty, T. J.; Smith, K. M., *J. Chem. Soc., Perkin Trans.* 1, 1992, p. 1377). In order to confirm the structure of the ring "A" and ring "B" modified derivatives, the vinyl group was transformed into a formyl substituent. Nuclear Overhauser enhancement (nOe) studies on the formyl derivatives confirmed the structural assignments for both of the starting materials. Interestingly, the NMR studies of the n-hexyl ether derivatives of ring "A" and ring "B" modified isomers (27, 35, 40 and 45; cis- and trans-) provided an independent verification of the precise (ring "A" or ring "B") isomer involved. As can be seen from FIG. 1, in the NMR spectrum (A, C) of the ring "B" reduced isomer 35 and 45 (as a mixture of diastereoisomers), there are two quartets for CH(O-hexyl)CH at 5.98 and 6.18 ppm, each integrating for one proton. However, in BPD derivatives 27 and 40, both of these protons of the diasteriomeric mixture resonate at 6.12 ppm as a broad multiplet, integrating for two protons. This is clear evidence that the chiral centers in 35 and 45 are closer to each other than they are in 27 and 40, and further reinforce the structural assignments. Interestingly, in the meso proton region (9.00–10.20 ppm) in 35 and 45 (FIGS. 1A and 1C) the meso protons are better separated than for the BPD derivatives 27 and 40.

In the porphyrin series, we have shown that certain porphyrins which were found to be poor photosensitizers as monomers, when converted to carbon-linked bis-porphyrins showed significant increase in photosensitizing efficacy ([a] Pandey, R. K.; Shiau, F. -Y.; Medforth, C. J.; Dougherty, T. J.; Smith, K. M., *Tetrahedron Lett.,* 1990, 31, p. 789; [b] Pandey, R. K.; Vicente, M. G. H.; Shiau, F. -Y.; Dougherty, T. J.; Smith, K. M., *Proc. SPIE,* 1991, 1426, p. 356).

Keeping this in mind, dimers 46 and 47 were prepared from 8-(1-hydroxyethyl)- and 3-(1-hydroxyethyl)-BPD, 24 and 32, respectively, by following our own methodology (Pandey, R. K.; Shiau, F. -Y.; Medforth, C. J.; Dougherty, T. J.; Smith, K. M., *Tetrahedron Lett.,* 1990, 31, p. 789). Thus, 24 and 32 were individually reacted with triflic acid, and the acid was quenched with pyridine before work up. The desired bis-porphyrins were isolated in about 50% yield.

Figure 2:
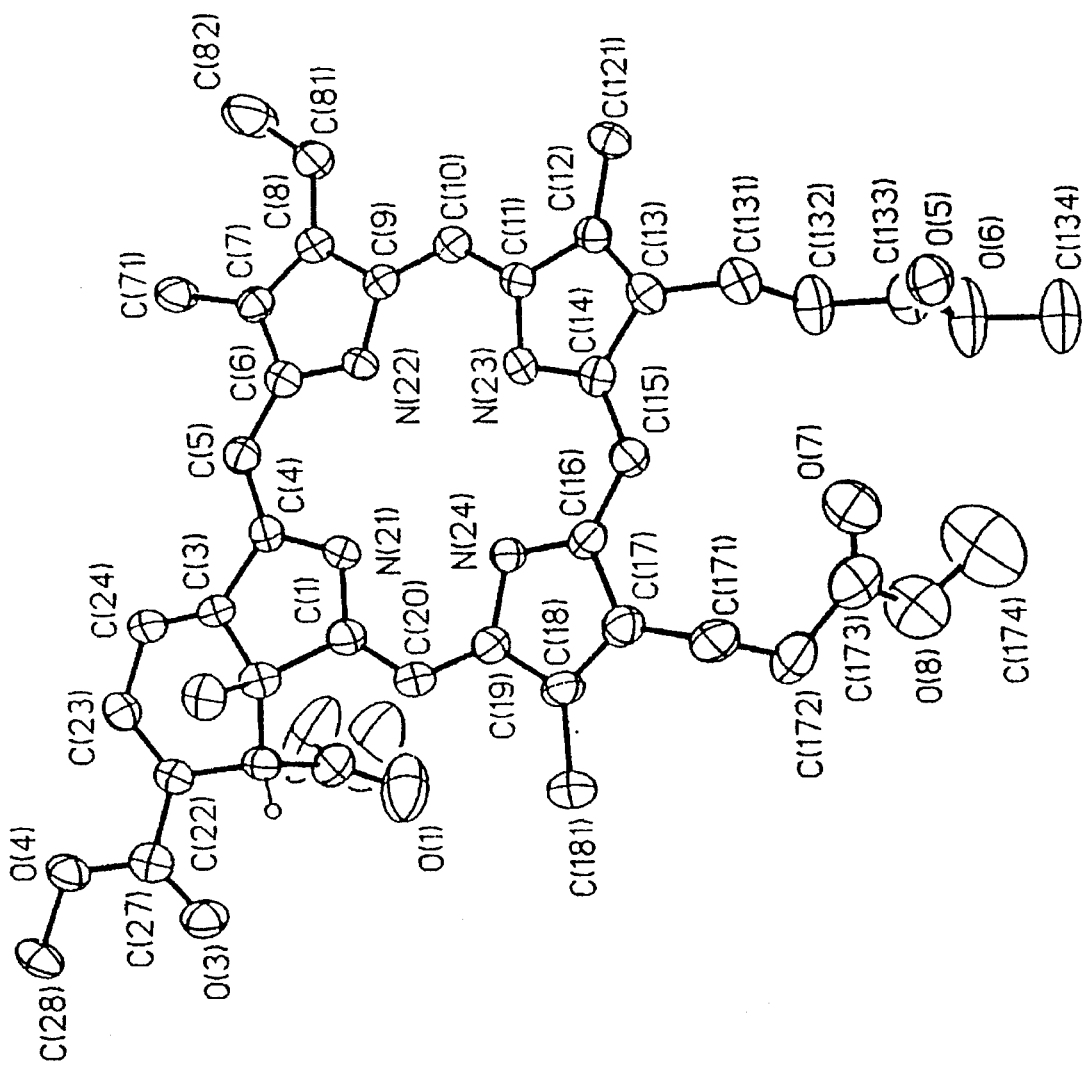
FIG. 2 shows a computer generated structure for compound 36. Ellipsoids are drawn for 50% occupancy.
Figure 3:
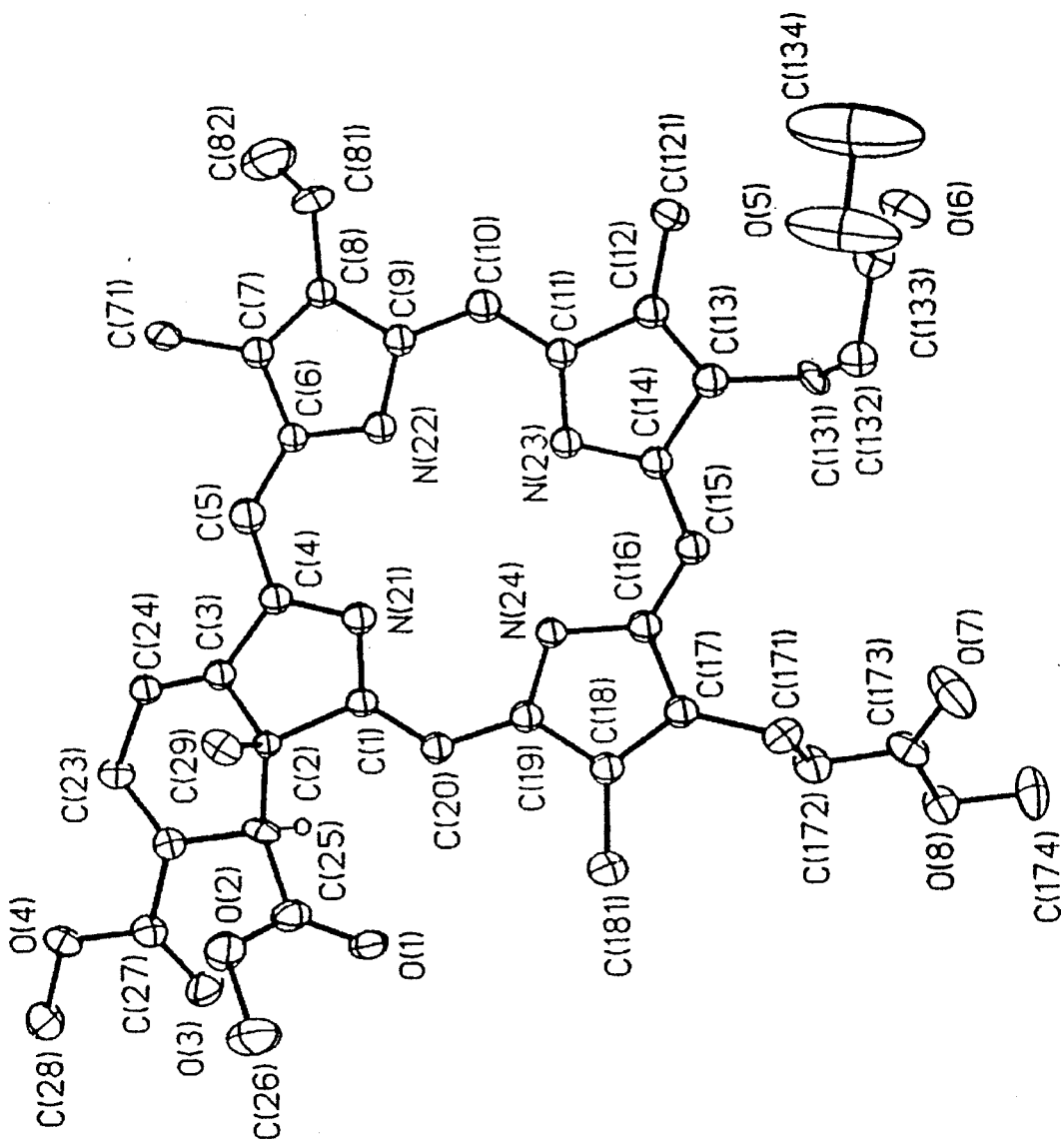
FIG. 3 shows a computer generated structure for compound 20. Ellipsoids are drawn for 50% occupancy.

The structure and stereochemistry of the cis and trans isomers of ring "A" reduced BPDs [as dimethyl esters 20 (cis isomer) and 36 (trans isomer)] were confirmed by single crystal X-ray studies. The atomic coordinates for both compounds are compiled in Tables 1 and 2. Full lists of bond lengths and angles, hydrogen atom coordinates, thermal parameters and further details of the structure determinations have been deposited at the Cambridge Crystallographic Data Centre. For details of the deposition scheme see 'Instructions for Authors', *J. Chem Soc., Perkin Trans.* 1 1994, issue 1. The molecular structures of the two isomeric forms are shown in FIGS. 2 and 3. Both structures clearly show the ring "A" adduct structure, evidenced by the site of the vinyl group in ring "B". The unsaturated character of the C(81)–C(82) bond is clearly shown by the short bond lengths of 1.291(7) and 1.363(12) Å in 36 and 20, respectively, The stereochemistry of the methoxycarbonyl and methyl substituents at C(21) and C(2) can clearly be elucidated as trans for 36 and cis for 20. The orientation of the double bonds in the fused six membered ring on pyrrole ring "A" can be delineated on the basis of the respective bond lengths. In 36 C(2)–C(21) [1.548(6) Å], C(21)–C(22) [1.519(6) Å], and C(23)–C(24) [1.456(8) Å] are obviously single bonds, while C(22)–C(23) [1.346(7) Å] and C(24)–C(3) [1.334(6) Å] have double bond character. A similar situation is found in the structure of 20. Both molecular structures differ somewhat in their macrocycle conformation. While in 36 the fused six-membered ring lies below the porphyrin macrocycle plane, this situation is reversed in 20. The average deviation of the porphyrin macrocycle atoms from their least-squares plane is not very significant, with 0.07 Å in the structure of 36. The structure of 20, however, shows a significant ring ruffling with an average deviation of the 24 core atoms of 0.14 Å. The larger ring distortion in the latter structure is also evidenced by an alternating displacement of the meso-positions by 0.24 Å above and below the mean plane; this is opposed to a meso-atom displacement of 0.06 Å found in 36.

All the new BPDs discussed here are being evaluated for their in vivo photosensitizing efficacy, and the final results will be reported elsewhere. Briefly, preliminary results indicate that among new photosensitizers, the (1-hexyloxy)ethyl derivatives 27, 35, 40 and 45 (as dimethyl esters) showed better anti-tumor activity than BPD-MA [mixture of 21 and 22, obtained from Quadralogic Technologies (QLT), Vancouver, Canada]. The hexyl ether derivatives 27, 35, 40, and 45 were found to be active at a dose of 1.0 mg/kg (mice were treated 3 h post i.v. injection of the drug). So far, only photosensitizer 40 has been studied in detail, and has shown excellent tumorcidal activity of the mice were treated at a dose of 5. 0 mg/kg 24 h post i.v. injection of the drug. Under similar conditions, BPD-MA did not show any activity. Photosensitizer 40 has also shown reduced skin phototoxicity compared with BPD-MA and Photofrin®. This work represents the first study in which a series of isomerically pure BPDs have been synthesized, characterized by single crystal X-ray studies, and evaluated for their in vivo PDT activity. We conclude that as with porphyrins ([a] Pandey, R. K.; Bellnier D. A.; Smith, K. M.; Dougherty, T. J.; *Photochem. Photobiol,* 1991, 53, 65; [b] Bellnier, D. A.; Henderson, B. W.; Pandey, R. K.; Potter, W. R.; Dougherty, T. J., *J. Photochem. Photobiol.* Part B: *Biol.* 1993, 20, p. 55), chlorins, and pheophorbides ([a] Pandey, R. K., Bellnier, D. A.; Smith, K. M.; Dougherty, T. J.; *Photochem. Photobiol,* 1991, 53, 65; [b] Bellnier, D. A.; Henderson, B. W.; Pandey, R. K.; Potter, W. R.; Dougherty, T. J., *J. Photochem Photobiol.* Part B: *Biol.* 1993, 20, p. 55) replacement of the vinyl group with a n-hexyl ether side chain in the BPD series results in a remarkable improvement in biological activity. On comparing the in vivo data among the cis- and trans isomers, it can be concluded that in the generic BPD series, the conformation of the modified ring (either ring "A" or ring "B") does not make a significant difference in biological activity. However, in general, the ring "A" reduced BPDs were found to be more active than the ring "B" modified analogues. Currently, we are modifying the polarity of these tetrapyrrole sensitizers further by replacing the methyl esters with aspartyl amide side chains, by varying the substituents, or by increasing the length of the carbon chain in alkyl ethers at peripheral position of the nucleus. These studies are in progress and will be reported in due course.

Experimental

M.p.s were measured on a Thomas/Bristoline microscopic hot stage apparatus and were uncorrected. Silica gel 60 (70–230 and 230–400 mesh, Merck) or neutral alumina (Merck; usually Brockmann Grade III, i. e., deactivated with 6% water) were used for column chromatography. Preparative thin layer chromatography was carried out on 20×20 cm glass plates coated with Merck G 254 silica gel (1 mm thick). Analytical thin layer chromatography (TLC) was performed using merck 60 F254 silica gel (precoated sheets, 0.2 mm thick). Reactions were monitored by TLC and spectrophotometry and were carried out under nitrogen and in the dark. $^1$HNMR spectra were obtained in deuteriochloroform solution at 300 MHz using a General Electric QE300 spectrometer; chemical shifts are expressed in ppm relative to chloroform (7.258 ppm). Elemental analyses were performed at the Midwest Microlab, Ltd., Indiana, USA. Unless stated otherwise, electronic absorption spectra were measured in dichloromethane solution using a Hewlett-Packard 8450A spectrophotometer. Mass spectra were obtained at the Mass Spectrometry Facility, University of California, San Francisco and at the Department of Biophysics, Roswell Park Cancer Institute, Buffalo.

Syntheses

3 -Acetylbenzoporphyrin Derivative (ring "B" modified) 31 (cis isomer) and 42 (trans isomer). 3-Acetyl-8-vinyldeuterophorphyrin-IX dimethyl ester 7 (100 mg, 0.165 mmol) was dissolved in 30 cm$^3$ of degased toluene. Dimethyl acetylenedicarboxylate ( 0.101 cm$^3$) was added rapidly and the reaction mixture was heated at 120° C. during 13 d, while being monitored by TLC. After evaporation to dryness under high vacuum, the major product was separated using preparative silica plates, eluting with 2% methanol in dichloromethane. The residue obtained after evaporating the extraction solvent was crystallized from dichloromethane/ n-hexane to give 18 in 40% yield (50 mg), m.p. 192°–194° C.; $\lambda_{max}$ 412 nm ($\epsilon$ 163,300), 506 (27,000), 536 (19,000), 616 (19,100), 670 (41,500); $\delta_H$ 9.82, 9.70, 9.53, 9.18 (each s, 1H, meso H); 7.39 (d, 2H, C$\underline{H}_2$); 7.26 (s, 1H, C$\underline{H}$CO$_2$Me); 4.25 (t, 2H, C$\underline{H}_2$CH$_2$CO$_2$Me); 4.15 (s, 3H, Me or OMe); 4.00 (t, 2H, C$\underline{H}_2$CH$_2$CO$_2$Me); 3.89, 3.80, 3.66, 3.65, 3.43, 3.38, 3.30 (each s, 3H, Me or OMe); 3.21, 3.13 (each t, 2H, $CH_2CH_2CO_2Me$); 2.15 (s, 3H, Me); −1.80 (broad s, 2H, NH). Treatment of 18 with triethylamine (0.3 cm$^3$) in dichloromethane (10.0 cm$^3$) overnight under $N_2$ gave the BPD 42 (trans isomer): M.p. 235°–237° C.; (Found: C, 65.58; H, 5.86; N, 7.15. $C_{42}H_{44}N_4O_9.H_2O$ requires: C, 65.76; H, 6.05; N, 7.30). $\lambda_{max}$ 418 nm (ε 84,800), 512 (8400), 516 (8100), 566 (8600), 636 (4600), 690 (20,100); $\delta_H$ 9.75, 9.73, 9.51, 9.17 (each s, 1H, meso H); 7.69 (dd, 1H, C—CH—CH); 7.36 (d, 1H, CH—CH); 4.76 (d, 1H, CH—$CO_2Me$); 4.24, 4.10 (each t, 2H, $CH_2CH_2CO_2Me$); 4.32 (s, 3H, Me or OMe); 3.93, 3.78, 3.66, 3.65, 3.42, 3.36, 3.31 (each s, 3H, Me and OMe); 3.19, 3.15 (each t, 2H, $CH_2CH_2CO_2Me$); 1.64 (s, 3H, Me); −1.99 (s, 2H, NH). Treatment of the intermediate (18) (20 mg) with DBU (3 drops) in dichloromethane (10.0 cm$^3$) at room temperature for 15 rain gave the BPD 31 (cis isomer) in quantitative yield, m.p. 238°–240° C.; $\lambda_{max}$ 420 nm (ε 70,700), 506 (9900), 574 (10,500), 638 (6700), 696 (24,600); $\delta_H$ 9.77, 9.59, 9.52, 9.22 (each s, 1H, meso H); 7.80, 7.44 (each d, 1H, CH=CH); 5.05 (s, 1H, CH—$CO_2Me$); 4.24, 4.11 (each t, 2H, $CH_2CH_2CO_2Me$); 3.98, 3.79, 3.65, 3.64, 3.42, 3.37, 3.34 (each s, 3H, Me and OMe); 3.18, 3.13 (each t, 2H, $CH_2CH_2$ $CO_2Me$); 3.02, 1.79 (ech s, 3H, Me); −1.72 (broad s, 2H, NH); HRMS, $C_{42}H_{44}N_4O_9$ requires: 748.3108; Found 748.3101.

By following the same approach, 23 and 37 (ring "A" modified) were obtained in 42 and 45% yield, respectively. 8-Acetylbenzoporphyrin Derivative 23 (cis isomer, ring "A" modified) –M.p. 242°–244° C.; $\lambda_{max}$ 422 nm (ε 72,000), 508 (10,000), 572 (11,500), 638 (7000), 696 (25,000); $\delta_H$ 10.29, 9.57, 9.44, 8.93 (each s, 1H, meso H); 7.80, 7.47 (each d, 1H, CH=CH); 5.05 (s, 1H, CH—$CO_2Me$); 4.27, 4.11 (each t, 2H, $CH_2CH_2CO_2Me$); 3.99, 3.70, 3.67, 3.60, 3.46, 3.35, 3.26 (each s, 3H, Me and OMe); 3.20, 3.13 (each t, 2H, $CH_2CH_2$ $CO_2Me$); 3.01 (s, 3H, COMe), 1.81 (s, 3H, Me); −1.70, −2.00 (each broad s, 1H, NH); HRMS, $C_{42}H_{44}N_4O_9$ requires: 748.3108; Found 748.3100. 8-Acetylbenzoporphyrin Derivative 3 7 (trans isomer, ring "A" modified) —M.p. 238°–240° C.; $\lambda_{max}$ 418 nm (ε 85,000), 514 (8000), 566 (8000), 636 (4600), 690 (22,000); $\delta_H$ 10.23, 9.56, 9.08, 8.93 (each s, 1H, meso H); 7.55,(dd, 1H, CH=CH); 6.90 (d, 1H, CH=CH); 4.58 (s, 1H, CH—$CO_2Me$); 4.25, 4.00 (each t, 2H, $CH_2CH_2CO_2Me$); 4.24, 3.97, 3.51, 3.45, 3.41 (each s, 3H, Me and OMe); 3.01 (s, 6H, Me); 3.24 (m, 4H, $CH_2CH_2$ $CO_2Me$); 3.17 (s, 3H, COMe), 1.43 (s, 3H, Me); −2.75 (broad s, 2H, NH).

8-(1-Hydroxyethyl)benzoporphyrin Derivative 24 (cis isomer, ring "A" modified)—8-Acetylbenzoporphyrin 23 (100 mg, 0.133 mmol) was dissolved in dichloromethane (50 cm$^3$) and cooled in an ice bath. A suspension of sodium borohydride (150 mg, 3 equiv) in cold methanol (5 cm$^3$) was added rapidly. After stirring the solution for 1 h at room temperature the reaction was found to be complete (TLC). Glacial acetic acid (2 cm$^3$) was added to quench the excess of sodium borohydride and the mixture was extracted with dichloromethane and washed with water to pH 7. The organic layer was separated, dried over $Na_2SO_4$. Evaporation of the solvent gave a residue which was crystallized from dichloromethane/n-hexane to afford the benzoporphyrin 24 (91 mg; 89% yield) as a mixture of diastereoisomers. M.p. 130°–135° C.; (Found: C 66.83, H 6.07, N 7.29, $C_{42}H_{46}N_4O_9$ requires: C 67.17, H 6.17, N 7.46). $\lambda_{max}$ 400 nm (ε 71,600), 578 (14,250), 622 (6300), 682 (29,800); $\delta_H$ 10.03, 10.01 (each s, 1H, meso H); 9.71 (s, 2H, meso H); 9.36, 9.35 (each s, 1H, meso H); 9.01 (s, 2H, meso H); 7.83 (d, 2H, CH=CH); 7.45 (d, 2H, CH=CH); 6.45 [q, 1H, CH(OH)]; 6.35 [q, 1H, CH(OH)]; 5.08 [s, 2H, $MeO_2CCHC(CO_2Me)$]; 4.32 (t, 4H, $CH_2CH_2CO_2Me$); 4.17 (t, 4H, $CH_2CH_2CO_2Me$); 3.99–3.38 (7 s, 36H, Me and OMe); 3.22 (t, 4H, $CH_2CH_2CO_2Me$); 3.16 (t, 4H, $CH_2CH_2CO_2Me$); 2.98 (s, 3H, Me); 2.96 (s, 3H, Me); 2.11 (d, 3H, $CHCH_3$); 2.10 (d, 3H, $CHCH_3$); 1.81 (s, 3H, Me); 1.79 (s, 3H, Me); −2.42 (broad s, 4H, NH).

3-(1,Hydroxyethyl)benzoporphyrin Derivative 32 (cis isomer, ring "B" modified) was prepared from 31 by following the procedure discussed for 24 and was isolated as a mixture of stereoisomers in 90% yield, m.p. 214°–215° C. (Found: C., 66.53; H, 6.19; N, 7.25,$C_{42}H_{46}N_4O_9.1.5$ $H_2O$ requires: C, 66.37; H, 6.49; N, 7.37). $\lambda_{max}$ 428 nm (ε 78,200), 578 (12,400), 624 (4300), 682 (30,400); $\delta_H$ 9.74, 9.72, 9.696, 9.692, 9.45 (each s, 1H, meso H); 9.37 (s, 2H, meso H); 9.28 (s, 1H, meso H); 7.82 (d, 2H, CH=CH); 7.44 (d, 2H, CH=CH); 6.58 [q, 1H, CH(OH)]; 6.48 [q, 1H, CH(OH)]; 5.08, 5.06 (each s, 1H, $CHCO_2Me$); 4.31 (t, 4H, $CH_2CH_2CO_2Me$); 4.17 (t, 4h, $CH_2CH_2CO_2Me$); 3.98–3.41 (6 s, 36H, Me and OMe); 3.20 (t, 4H, $CH_2CH_2CO_2Me$); 3.15 (t, 4H, $CH_2CH_2CO_2Me$); 2.88, 2.89 (each s, 3H, Me); 2.25, 2.19 (each d, 3H, CH(OH)Me); 1.82, 1.81 (each s, 3H, Me); −2.37, −2.33 (each broad s, 2H, NH).

8-vinylbenzoporphyrin Derivative 20 (cis isomer, ring "A" modified). —Benzoporphyrin 24 (90 mg, 0.12 mmol) was dissolved in o-dichlorobenzene (50 cm$^3$) and heated to 150° C. before addition of p-toluenesulphonic acid (194 mg, 1.02 mmol). Nitrogen was bubbled through the solution during 45 min, and after cooling the solution was diluted with dichloromethane and washed with water (3×250 cm$^3$). The organic phase was dried over $Na_2SO_4$, filtered, and treated with excess ethereal diazomethane. After evaporation of the solvents, compound 20 was crystallized from dichloromethane/n-hexane and isolated in 93% yield (82 mg), m.p. 134°–136° C.; (Found: C, 68.83; H, 6.05; N, 7.39,$C_{42}H_{44}N_4O_8$ requires: C, 68.82; H, 6.05; N, 7.64). $\lambda_{max}$ 418 nm (ε 75,600), 580 (11,500), 626 (3620), 688 (28,500); $\delta_H$ 9.83, 9.69, 9.42, 8.99, (each s, 1H, meso H); 8.16 (dd, 1H, CH=$CH_2$); 7.82 (d, 1H, CH=CH); 7.44 (d, 1H, CH=CH); 6.35 (d, 1H, CH=$CH_2$); 6.17 (d, 1H, CH=$CH_2$); 5.07 (s, 1H, $CHCO_2Me$); 4.31, 4.17 (each t, 2H, $CH_2CH_2CO_2Me$); 3.99, 3.67, 3.66, 3.56, 3.49, 3.39 (each s, 3H, Me and OMe); 3.21, 3.15 (each t, 2H, $CH_2CH_2CO_2Me$); 2.96 (s 3H, Me); 1.81 (s, 3H, Me); −2.31 (broad s, 2H, NH).

3-Vinylbenzoporphyrin Derivative 28 (cis isomer, ring "B" modified)—Starting from 32 (80 mg), benzoporphyrin 28 was synthesized in 93% yield by following the procedure reported above for compound 20. M.p. 212°–214° C. (Found: C, 67.42; H, 6.20, N, 7.95. $C_{42}H_{44}N_4O_8H_2O$: requires C, 67.17; H, 6.17; N, 7.46). $\lambda_{max}$ 430 nm (ε 69,100), 582 (13,100), 628 (6050), 690 (29,450); $\delta_H$ 9.76, 9.69, 9.36, 9.14 (each s, 1H, meso H); 8.12 (dd, 1H, CH=$CH_2$); 7.82 (d, 1H, CH=CH); 7.45 (d, 1H, CH=CH); 6.37 (d, 1H, CH=$CH_2$) 6.17 (d, 1H, CH=$CH_2$); 5.06 (s, 1H, $CHCO_2Me$); 4.32, 4.18 (each t, 2H, $CH_2CH_2CO_2Me$); 3.98, 3.66, 3.64, 3.60, 3.48, 3.42 (each s, 3H, Me and OMe); 3.20, 3.16 (each t, 2H, $CH_2CH_2CO_2Me$); 2.94 (s, 3H, Me); 1.78 (s, 3H, Me); −2.29 (broad s, 2H, NH).

8-Vinylbenzoporphyrin Derivative 36 (trans isomer, ring "A" modified). —8-Acetylbenzoporphyrin derivative 37 (100 mg) was first reduced to the (1-hydroxyethyl) derivative 38 by treatment with sodium borohydride (150 mg), as described for compound 24. Next, 38 was heated with p-toluene sulphonic acid (200 mg) in refluxing o-dichlorobenzene (50 cm$^3$) to give 79 mg (80%) of the title vinyl compound, m.p. 138°–142° C. $\lambda_{max}$ 418 nm (ε 86,000), 570 (14,500), 620 (3,500), 680 (28,000); $\delta_H$ 9.78 (s, 2H, meso-H), 9.43, 9.30 (each s, 1H, meso H); 8.18 (dd, 1H, C$\underline{\text{H}}$=CH$_2$); 7.84 (d, 1H, C$\underline{\text{H}}$=CH); 7.44 (d, 1H, C$\underline{\text{H}}$=CH); 6.34 (d, 1H, CH=C$\underline{\text{H}}_2$); 6.15 (d, 1H, CH=C$\underline{\text{H}}_2$); 5.00 (s, 1H, C$\underline{\text{H}}$CO$_2$Me); 4.32, 4.22 (each t, 2H, C$\underline{\text{H}}_2$CH$_2$CO$_2$Me); 4.20, 3.86, 3.66, 3.64, 3.50, 3.42, 294, 1.80 (each s, 3H, Me and OMe); 3.16, 3.12 (each t, 2H, CH$_2$C$\underline{\text{H}}_2$CO$_2$Me); −2.30 (broad s, 2H, NH); HRMS, C$_{42}$H$_{44}$N$_4$O$_8$ requires: 732.3153; Found 732.3150.

Bis-Benzoporphyrin 46 (cis isomer)—Benzoporphyrin 24 (28 mg, 0.037 mmol) was dissolved in dichloromethane (10 cm$^3$). Trifluoromethanesulphonic acid (0.4 cm$^3$) was added and the mixture was stirred at room temperature under nitrogen for 3 h. Pyridine (1.0 cm$^3$) was then added and stirring was continued for another 30 min. The reaction mixture was extracted with dichloromethane and the organic phase was washed with water (3×200 cm$^3$), dried over Na$_2$SO$_4$, filtered, and evaporated to dryness. The residue was purified by preparative chromatography on silica gel plates, eluting with 2% methanol in dichloromethane. The major product, 46, was isolated in 44% yield (11.8 mg), as a mixture of stereoisomers, m.p. 184°–186° C.; $\lambda_{max}$ 426 nm (ε 142,200), 580 (30,900), 622 (17,600), 682 (55,300); δ$_H$ (gross diastereomeric mixture) 10.32–8.28 (15 s, 8H, meso H); 7.85–7.80 (m, 2H, CH=CH); 7.50–7.18 (m, 4H, MeO$_2$C—CH=CH); 6.5–5.6 (4m, 1H, CH—Me); 5.12, 5.10 (each s, 1H, MeO$_2$CC$\underline{\text{H}}$); 5.06 (s, 1H, MeO$_2$CC$\underline{\text{H}}$); 4.33, 4.12 (each m, total 32H, C$\underline{\text{H}}_2$CH$_2$CO$_2$Me); 4.00, 4.01, 3.98, 3.97 (each s, 24H, Me or OMe); 3.81, 3.67, 3.66, 3.65, 3.62, 3.57, 3.52, 3.51, 3.48, 3.47 (each s, total 108H, Me or OMe); 3.26, 3.23, 3.22 (each s, total 36H, Me or OMe); 2.97–2.93 (m, 32H, CH$_2$C$\underline{\text{H}}_2$CO$_2$Me); 2.89, 2.61, 2.47, 2.07 (each d, 3H, CH M$\underline{\text{e}}$); 1.86, 1.84, 1.78 (each s, total 24H, Me); −2.20, −2.35, −2.49 (broad s, total 16H, NH); LRMS, Found [M+H]$^+$: 1465.4, C$_{84}$H$_{88}$N$_8$O$_{16}$ requires: 1464.6.

Bis-Benzoporphyrin 47 (cis isomer) —Starting from 32, bis-benzoporphyrin 47 was obtained by the procedure used for the foregoing dimer and was isolated in 58% yield. M.p. 195°–197° C. δ$_H$ (gross diastereomeric mixture) 9.95, 9.94, 9.76, 9.75, 9.71, 9.68, 9.66, 9.65, 9.42, 9.39, 9.38. 9.37, 9.33, 9.30, 8.28, 8.22 (each s, total 32H, meso H); 7.87–7.78 (m, 16H, CH=CH); 7.49–7.43 (m, 16H, CH=CH); 6.01 (q, 2H, C$\underline{\text{H}}$Me); 5.90 (q, 2H, C$\underline{\text{H}}$Me); 5.22–5.05 (6s, total 8H, MeO$_2$CC$\underline{\text{H}}$); 4.34, 4.16 (m, total 32H, C$\underline{\text{H}}_2$CH$_2$CO$_2$Me); 4.02, 4.01, 3.99, 3.98, 3.94, 3.92, 3.80 (each s, total 48H, 16 Me or OMe); 3.67, 3.66, 3.65, 3.64 (each s, total 54H, 18 Me or OMe); 3.49, 3.47 (each s, total 36H, Me or OMe); 3.37, 3.27 (each d, total 12H, CHM$\underline{\text{e}}$); 3.21–3.15 (m, total 38H, CH$_2$C$\underline{\text{H}}_2$CO$_2$Me and 6Me or OMe); 2.99, 2.92, 2.89, 2.85, 2.83 (each s, total 18H, Me); 2.67 (t, total 8H, CH$_2$C$\underline{\text{H}}_2$CO$_2$Me); 2.60 (t, total 4H, CH$_2$C$\underline{\text{H}}_2$CO$_2$Me); 1.94, 1.84, 1.79, 1.77, 1.65 (each total 18H, 6Me); −2.31 (broad s, 16H, NH); LRMS, Found [M+H]$^+$: 1465.8. C$_{84}$H$_{88}$N$_8$O$_{16}$ requires 1464.6.

8-Ethylbenzoporphyrin Derivative 25 (ring "A" modified, cis isomer)—3-Vinyl-8-ethyldeuteroporphyrin-IX dimethyl ester 13 (400 mg, 0.675 mmol) was dissolved in degased toluene (130 cm$^3$). Dimethyl acetylenedicarboxylate (0.42 cm$^3$, 3.37 mmol) was added and the solution was stirred at 120° C. under a N$_2$ atmosphere for 5 d. After evaporation of the solvent, the intermediate (16) was isolated by a combination of silica gel column chromatography, eluting with 1.5% methanol in dichloromethane, followed by silica gel preparative plates eluting with the same solvent mixture. The intermediate Diels Alder adduct (16), after crystallization from dichloromethane/n-hexane, was obtained in 43% yield (173 mg) as a brown crystalline solid, m.p. 113°–115° C-(Found: C, 68.42; H, 6.20; N, 7.58. C$_{42}$H$_{46}$N$_4$O$_8$ requires: C, 68.63; H, 6.31; N, 7.62). $\lambda_{max}$ 400 nm (ε 191,900), 498 (21,350), 502 (21,300), 532 (22,100), 598 (14,200), 626 (13,200), 654 (47,200); δ$_H$ 9.77, 9.71, 9.34, 9.10 (each s, 1H, meso H); 7.39 (dd, 2H, C$\underline{\text{H}}$=CH); 7.29 (d, 1H, CH$_2$C$\underline{\text{H}}$); 4.35, 4.22 (each t, 2H, C$\underline{\text{H}}_2$CH$_2$CO$_2$Me); 4.02, 3.90 (each s, 3H, Me or OMe); 4.01 (q, 2H, C$\underline{\text{H}}_2$CH$_3$); 3.67 (s, 6H, Me or OMe); 3.51, 3.48, 3.43 (each s, 3H, Me or OMe); 3.22, 3.19 (each t, 2H, CH$_2$C$\underline{\text{H}}_2$CO$_2$Me); 2.09 (s, 3H, Me); 1.79 (t, 3H, CH$_2$C$\underline{\text{H}}_3$); −2.66, −2.64 (each broad s, 1H, NH). HRMS, Found: 734.3409. C$_{42}$H$_{46}$N$_4$O$_8$ requires: 734.3315.

The intermediate 16 (120 mg, 0.16 mmol) was dissolved in dichloromethane (40 cm$^3$) and DBU (5 drops) was added; the reaction mixture was kept at room temperature for 15 min, monitored by spectrophotometry. The solution was then evaporated to dryness and the desired compound 25 was recrystallized in dichloromethane/n-hexane to give 107 mg (89% yield), m.p. 125°–130° C. (Found: C, 66.60; H, 6.31; N, 7.51. C$_{42}$H$_{46}$N$_4$O$_8$H$_2$O requires: C, 66.99; H, 6.42; N, 7.44). $\lambda_{max}$ 416 nm (ε 72,300), 580 (17,400), 620 (11,100), 680 (31,200); δ$_H$ 9.72, 9.70, 9.38, 9.00 (each s, 1H, meso H); 7.83, 7.44 (each d, 1H, CH=CH); 5.08 (s, 1H, C$\underline{\text{H}}$CO$_2$Me); 4.33, 4.19 (each t, 2H, C$\underline{\text{H}}_2$CH$_2$CO$_2$Me); 3.99 (s, 3H, Me or OMe); 3.98 (q, 2H, C$\underline{\text{H}}_2$CH$_3$); 3.68 (s, 6H, Me or OMe); 3.50, 3.46, 3.43 (each s, 3H, Me or OMe); 3.22, 3.19 (each t, 2H, CH$_2$C$\underline{\text{H}}_2$CO$_2$Me); 2.94 (s, 3H, Me); 1.80 (s, 3H, Me); 1.77 (t, 3H, CH$_2$C$\underline{\text{H}}_3$ ); −2.46 (broad s, 1H, NH). HRMS, Found: 734.3323. C$_{42}$H$_{46}$N$_4$O$_8$ requires: 734.3315.

2-Ethylbenzoporphyrin Derivative 33 (ring "B" modified, cis isomer) was synthesized from porphyrin 12 by the procedure discussed above for 25,and was isolated in 52% yield, m.p. 178°–181° C. (Found: C, 65.70; H, 6.75; N, 7.62. C$_{42}$H$_{46}$N$_4$O$_8$. 2H$_2$O requires: C, 65.42; H, 6.53; N, 7.26). $\lambda_{max}$ 414 nm (ε 54,500), 580 (11,200), 620 (5300), 680 (23,000); δ$_H$ 9.71, 9.70, 9.39, 8.99 (each s, 1H, meso H); 7.83, 7.44 (each d, 1H, CH=CH); 5.07 (s, 1H, C$\underline{\text{H}}$CO$_2$Me); 4.33, 4.19 (each t, 2H, C$\underline{\text{H}}_2$CH$_2$CO$_2$Me); 3.99 (s, 3H, Me or OMe); 3.92 (q, 2H, C$\underline{\text{H}}_2$CH$_3$); 3.65, 3.64, 3.52, 3.49, 3.42 (each s, 3H, Me or OMe); 3.20, 3.16 (each t, 2H, CH$_2$C$\underline{\text{H}}_2$CO$_2$Me); 2.90 (s, 3H, Me); 1.80 (s, 3H, Me); 1.78 (t, 3H, CH$_2$C$\underline{\text{H}}_3$); −2.46, −2.60 (each broad s, 1H, NH).HRMS, Found: 734.3307. C$_{42}$H$_{46}$N$_4$O$_8$ requires 734.3315.

2-Ethylbenzoporphyrin Derivative 44 (ring "B" modified, trans isomer)—The intermediate Diels-Alder adduct 19 obtained after the reaction of 12 with DMAD [Compound 19, m.p. 174°–176° C. (Found: C, 68.59; H, 6.39; N, 7.57. C$_{42}$H$_{46}$N$_4$O$_8$ requires: C, 68.63; H, 6.31; N, 7.62). $\lambda_{max}$ 400 nm (ε 183,800), 504 (9500), 532 (10,600), 598 (2600), 626 (1700), 654 (38,400); δ$_H$ 9.77, 9.71, 9.35, 9.12 (each s, 1H, meso H) ; 7.40 (dd, 2H, C$\underline{\text{H}}$=CH); 7.29 (d, 1H, CH$_2$C$\underline{\text{H}}$); 4.34, 4.20 (each t, 2H, C$\underline{\text{H}}_2$CH$_2$CO$_2$Me); 4.02, 3.90 (each s, 3H, Me or OMe); 3.96 (q, 2H, C$\underline{\text{H}}_2$CH$_3$); 3.67, 3.66, 3.55, 3.51, 3.43 (each s, 3H, Me or OMe); 3.22, 3.17 (each t, 2H, CH$_2$C$\underline{\text{H}}_2$CO$_2$Me); 2.08 (s, 3H, Me); 1.78 (t, 3H, CH$_2$C$\underline{\text{H}}_3$); −2.70, −2.65 (each broad s, 1H, NH)] was dissolved in dichloromethane and then treated with triethylamine. The title compound was isolated in 95% yield, m.p. 224°–226° C. (Found: C, 68.71, H, 6.36, N, 7.54. C$_{42}$H$_{46}$N$_4$O$_8$ requires: C, 68.63; H, 6.31; N, 7.62). $\lambda_{max}$ 414 nm 78,300), 570 (14,100), 614 (4700), 672 (23,500); δ$_H$ 9.77 (s, 2H, meso H); 9.42, 9.29 (each s, 1H, meso H); 7.75, 7.43 (each d, 1H, MeO$_2$CC=CHCH); 4.86 (d, 1H, C$\underline{\text{H}}$CO$_2$Me); 4.35, 4.20 (each t, 2H, C$\underline{\text{H}}_2$CH$_2$CO$_2$Me); 4.27, 3.94, 3.66, 3.65, 3.54, 3.52, 3.44 (each s, 3H, Me or OMe); 3.94 (q, 2H, C$\underline{\text{H}}_2$CH$_3$); 3.20, 3.15 (each t, 2H, CH$_2$C$\underline{\text{H}}_2$CO$_2$Me); 1.80 (t, 3H, CH$_2$C$\underline{\text{H}}_3$); 1.64 (s, 3H, Me); −2.62, −2.69 (each broad s, 1H, NH).

8-(1-Hexyloxyethyl)benzoporphyrin Derivative 27 (ring "A" modified, cis isomer)—BPD 20 (30 mg, 0.041 retool) was stirred with 30% hydrogen bromide/acetic acid (3 cm$^3$) under an atmosphere of N$_2$ at room temperature for 2 h. After evaporation to dryness, n-hexanol (3.0 cm$^3$, 23.9 mmol) was rapidly added to the green bromoethyl derivative and the solution was stirred at room temperature for 2 h. The reaction mixture was then diluted with dichloromethane (150 cm$^3$) and the organic phase washed with water, saturated aqueous sodium hydrogen carbonate solution and water again. After drying over Na$_2$SO$_4$, filtration and evaporation, the residue was treated with excess ethereal diazomethane and the solvent was evaporated. The residual n-hexanol was removed under high vacuum. The residue was purified by preparative TLC, eluting with 1.5% methanol in dichloromethane as mobile phase. Two bands were separated; the most mobile band, a minor component, was not identified. The more polar fraction was characterized as the title compound 27, obtained in 50% yield (17 mg). $\lambda_{max}$ 422 nm ($\epsilon$ 62,100), 576 (16,150), 576 (16,150), 622 (9800), 682 (27,200); $\delta_H$ 10.18, 10.17, 9.72, 9.41, 9.00,(each s, total 4H, meso H); 7.82, 7.43 (each d, 1H, MeCO$_2$C=CHCH); 6.02 (q, 1H, —CH(CH$_3$)—O); 5.08 (s, 1H, MeO$_2$CCHC—CO$_2$Me); 4.33, 4.19 (each t, 2H, CH$_2$CH$_2$CO$_2$Me); 3.99, 3.68, 3.54, 3.50, 3.46, 3.42, 2.94, 2.93 (each s, total 24H, Me, OMe); 3.23, 3.16 (each t, 2H, CH$_2$CH$_2$CO$_2$Me); 2.16 (d, 3H, CHMe); 2.00–0.76 (m, total 13 H, (CH$_2$)$_5$—Me); −2.40 (broad s, 2H, NH). HRMS, Found: 834.4210. C$_{48}$H$_{58}$N$_4$O$_9$ requires: 834.4203.

3-(1-Hexyloxyethyl)benzoporphyrin Derivative 35 (ring "B" modified, cis isomer)—This BPD was synthesized from 28 by following the method described above, and was obtained in 50% yield as a mixture of diastereoisomers, m.p. 94°–95° C.; $\lambda_{max}$ 426 nm ($\epsilon$ 63,200), 578 (17,300), 624 (10,700), 682 (30,700); $\delta_H$ 9.75, 9.73, 9.69, 9.45, 9.38, 9.15 (each s, total 8H, meso H); 7.83, 7.45 (each pseudo t, 4H, MeO$_2$CC=CH—CH); 6.21, 5.95 (each q, 1H, CHO-hexyl); 5.07 (s, 2H, CHCO$_2$Me); 4.32, 4.19 (each t, 8H, CH$_2$CH$_2$CO$_2$Me); 3.99 (s, 6H, Me); 3.65, 3.64, 3.48, 3.47, 3.42, 2.90 (each s, 42H, Me, OMe); 3.21, 3.16 (each t, total 8H, CH$_2$CH$_2$CO$_2$Me); 2.22, 2.09 (each d, 3H, —CH(CH$_3$) O-hexyl); 1.85–0.73 (m, 26H, Me and O-hexyl); −2.30, −2.40 (broad s, 4H, NH). HRMS, Found: 834.4206. C$_{48}$H$_{58}$N$_4$O$_9$ requires: 834.4203. An unidentified minor component was also isolated, but not further characterized.

8-(1-Hexyloxyethyl)benzoporphyrin Derivative 40 (ring "A" modified, trans isomer)—BPD 36 (30 mg, 0.041 mmol) was stirred with 30% hydrogen bromide/acetic acid (3 cm$^3$) under a N$_2$ atmosphere, following the procedure as discussed above, and the title compound was isolated in 50% yield, m.p. <60° C. (Found: C, 68.53; H, 7.05; N, 6.54. C$_{48}$H$_{58}$N$_4$O$_9$0.5H$_2$O requires: C, 68.31; H, 7.04; N, 6.64 ); $\lambda_{max}$ 426 ($\epsilon$ 69,000), 498 (8500), 568 (16,300), 616 (8200), 674 (24,800); $\delta_H$ 10.22, 9.78, 9.45, 9.28 (each s, 1H, meso H); 7.76, 7.44 (each d, 1H, MeCO$_2$C=CHCH); 6.05 [q, 1H, —CH(CH$_3$)—O]; 4.84 (d, 1H, MeO$_2$CCHCCO$_2$Me); 4.36 (t, 2H, CH$_2$CH$_2$CO$_2$Me); 4.27 (s, 3H, Me); 4.21 (t, 2H, CH$_2$CH$_2$CO$_2$Me); 4.92– 3.44 (each s, total 18H, Me, OMe); 3.21 (t, 2H, CH$_2$CH$_2$CO$_2$Me); 3.18 (t, 2H, CH$_2$CH$_2$CO$_2$Me); 2.17–0.76 [m, total 19H, Me and (CH$_2$)$_5$Me]; −2.57 (broad s, 2H, NH). HRMS, Found: 834.4213. C$_{48}$H$_{58}$N$_4$O$_9$ requires: 834.4203.

3-(1-Hexyloxyethyl)benzoporphyrin Derivative 45 (ring "B" reduced, trans isomer)—3-Vinyl-BPD 41 (20 mg, 0.03 mmol) was converted into the title compound by following the procedure as discussed for the foregoing BPD and was isolated in 55% yield as a mixture of diastereoisomers, m.p. 95°–97° C. $\lambda_{max}$ 422 ($\epsilon$ 69,400), 568 (8600), 568 (16,800), 618 (9200), 676 (25,200); $\delta_H$ 9.83, 9.79, 9.73, 9.72, 9.66 (each 1s, 5H, meso H); 9.39, 9.40, 9.41 (each s 1H, meso H); 7.73–7.77 (m, 2H, MeO$_2$CC=CHCH); 7.44 (d, 2H, MeO$_2$C—C=CHCH); 6.13 (q, 1H, CH—O-hexyl); 5.95 (q, 1H, CH— O-hexyl); 4.87 (m, 2H, MeO$_2$CCHC—CO$_2$Me); 4.34 (t, 4H, CH$_2$CH$_2$CO$_2$Me); 4.34 (s, 3H, Me); 4.29 (s, 3H, Me); 4.19 (t, 4H, CH$_2$CH$_2$CO$_2$Me); 3.94–3.44 (8s, 36H, Me, OMe); 3.22 (t, 4H, CH$_2$CH$_2$CO$_2$Me); 3.17 (t, 4H, CH$_2$CH$_2$CO$_2$Me); 2.23 (d, 3H, —CH(CH$_3$)—O-hexyl); 2.18 (d, 3H, CH(CH$_3$)—O-hexyl); 1.73–0.72 (m, 32H, Me and O-hexyl); −2.54 (broad s, 2H, NH); −2.61 (broad s, 2H, NH). HRMS, Found: 834. 4228. C$_{48}$H$_{58}$N$_4$O$_9$ requires: 834.4203.

8-Formylbenzoporphyrin Derivative 26 (ring "A" modified, cis isomer)—8-Vinylbenzoporphyrin derivative 20 (80 mg, 0.11 mmol) was dissolved in tetrahydrofuran (40 cm$^3$). Osmium tetraoxide (20 mg) in carbon tetrachloride (1 cm$^3$) and sodium periodate (320 mg) in water (15 cm$^3$) and dioxane (15 cm$^3$) were added. The mixture was stirred under a N$_2$ atmosphere for 45 min at room temperature, after which the reaction was judged to be complete (spectrophotometry, disappearance of peak at 680 and appearance of new peak at 689 nm in dichloromethane). The mixture was diluted with dichloromethane (200 cm$^3$), washed with water (3×200 cm$^3$), and the organic phase was dried (Na$_2$SO$_4$) and evaporated to give a residue which was chromatographed on silica gel plates, eluting with 5% methanol in dichloromethane. The major band was collected and the product was crystallized from dichloromethane/n-hexane to give 65 mg (80% yield) of the title compound, m.p. 250°–252° C. $\lambda_{max}$ 434 ($\epsilon$ 85,000), 514 (8000), 566 (7200), 638 (6000), 696 (24,000); $\delta_H$ 11.27 (s, 1H, CHO); 10.06, 9.48, 9.02, 8.74 (each s, 1H, meso H); 7.54 (dd, 1H, MeO$_2$CC=CHCH); 6.86 (d, 1H, MeO$_2$O$_2$CC=CHCH); 4.54 (d, 1H, CHCO$_2$Me); 4.06 (m, 4H, CH$_2$CH$_2$CO$_2$Me); 4.24, 3.99, 3.43, 3.28 (each s, 3H, Me or OMe); 3.68 (s, 9H, Me, OMe); 3.20, 3.12 (each t, 2H, CH$_2$CH$_2$CO$_2$Me); 1.37 (s, 3H, Me); −2.15 (broad s, 2H, NH). HRMS, Found: 734.2948. C$_{41}$H$_{42}$N$_4$O$_9$ requires: 734.2945.

3-Formylbenzoporphyrin Derivative 34 (ring "B" modified, cis isomer)—3-Vinylbenzoporphyrin derivative 28 (80 mg, 0.11 mmol) was reacted with osmium tetraoxide/sodium periodate as described above for compound 26. The title compound was isolated in 82% yield (66 mg), m.p. 242°–245° C. $\lambda_{max}$ 434 ($\epsilon$ 85,000), 512 (8500), 566 (7500), 638 (6500), 696 (24,000); $\delta_H$ 11.48 (s, 1H, CHO); 9.78, 9.70, 9.45, 9.05 (each s, 1H, meso H); 7.66 (dd, 1H, C=CHCH); 7.32 (d, 1H, C=CHCH); 4.69 (d, 1H, CHCO$_2$Me); 4.23, 4.09 (each t, 2H, CH$_2$CH$_2$CO$_2$Me); 4.34, 3.94, 3.82, 3.69, 3.65, 3.39, 3.30 (each s, 3H, Me or OMe); 3.19–3.09 (m, 4H, CH$_2$CH$_2$CO$_2$Me); 1.65 (s, 3H, Me); −1.60, −1.80 (each broad s, 1H, NH). HRMS, Found: 734.3000. C$_{41}$H$_{42}$N$_4$O$_9$ requires: 734.2945.

Crystallography

Crystals of 36 were grown by slow diffusion of n-hexane into a concentrated solution of the porphyrin in dichloromethane. The cis compound 20 was crystallized from chloroform/n-hexane. The crystals were mounted on a glass fiber using the method described by Hope, H., ACS Symp. Ser., 1987, 357, 257). Crystal Data. Compound 36. —$C_{42}H_{44}N_4O_8$, M=732.8, triclinic, a=10.695(6), b=13.895(5), c=14.188(5) Å, α=71.22(3), β=71.57(4), γ=72.41(4)°, U=1846 Å$^3$ (by least-squares refinement on diffractometer angles for 19 automatically centered reflections, λ=0.7107 Å), space group P$\bar{1}$, Z=2, $D_c$=1.318 g cm$^{-3}$ F (000)=776. Red block, 0.4×0.35×0.31 mm, μ(Mo—Kα)= 0.092 mm$^{-1}$. Compound 20. —$C_{42}H_{44}N_4O_8$, M=732.8, triclinic, a=8.467(4), b=13.863(6), c=15.718(10) Å, α=89.33(4), β=85.04(4), γ=81 31 (4)°, U=1817 Å$^3$ (by least-squares refinement on diffractometer angles for 22 automatically centered reflections, λ=1.54178 Å), space group P$\bar{1}$, Z=2, $D_c$=1.339 g cm$^{-3}$, F. (000)=776. Brown parallelepiped, 0.21×0.15×0.05 mm, μ(Cu—Kα)=0.763 mm$^{-1}$.

Data Collection and Processing. Compound 36—Siemens R3m/V diffractometer, 130K, ω mode with ω scan range 2.0°. ω scan speed 6.01° min$^{-1}$, graphite-monochromated Mo-Kα radiation; 7665 reflections measured (0<2θ≤52°, ±h, ±k, +1), giving 4194 reflections with F>4σ(F). The intensities are corrected for Lorentz, polarization, and absorption effects; extinction was disregarded.

Compound 20. —Siemens P4 diffractometer equipped with a rotating anode operating at 50 kV and 300 mA, 120K, 2θ–θ mode with a scan range of 2.2° plus Kα separation, scan speed 29.3° min$^{-1}$, Cu—Kα radiation; 4567 reflections measured (0<2θ≤108.5°, ±h, ±k, +1), giving 3224 reflections with F>4σ(F).

Structure Analysis and Refinement. Compound 36. The structure was solved by direct methods followed by full-matrix least-squares refinement with all non-hydrogen atoms anisotropic and hydrogens in calculated positions using a riding model. The weighting scheme used was $w^{-1}=\sigma^2(F)+0.0002F^2$; refinement of 487 parameters gave final R and $R_w$ values of 0.083 and 0.079. Programs and computers used and sources of scattering factor data are given in Senge, M. O.; Hope, H.; Smith, K. M., [1993] J. Chem. Soc., Perkin Trans 2, p. 11.

Compound 20. —Only the peripheral side chain non-hydrogen atoms were refined with anisotropic thermal parameters. The weighting scheme used was $w^{-1}=\sigma^2(F)+0.1260F^2$; refinement of 362 parameters gave final R and $R_W$ values of 0.111 and 0.133. Structure solution and other refinement details were as reported for compound 36.

Mass spectrometric analyses were performed by the University of California, San Francisco, Mass Spectrometry (A. L. Burlingame, Director) supported by the Biomedical Research Technology Program of the National Center for Research Resources, NIH NCRR BRTP 01614, and at the Department of Biophysics, Roswell Park Cancer Institute, Buffalo.

Tumor Response and Foot Response Experiments: For tumor response experiments (see Table 3), a 1mm$^3$ piece of SMT-F tumor from a donor DBA/2 Ha-DD mouse was implanted subcutaneously with a trocar into the axilla of a 5–7 week old female DBA/2 Ha-DD mouse. When the tumor had grown to about 4mm diameter, mice were injected intravenously (i.v.) with photosensitizers at various doses. At various time after injection, mice were restrained in Plexiglas® holders and each tumor was illuminated with 135 J/cm$^2$ light from a dye laser 171 (spectra physics). The light dose rate was 75 mW/cm$^2$ as measured with a PTR Optics monochromator. The percentage of short term control (non-palpable tumors) was recorded daily. For our study 6 mice/group were used.

Foot-response experiments were carried out on 5–7 week old female DBA/2 HaDD mice. Sensitizers were injected i.v. at the following doses: Photofrin® in normal saline, BPD (industrial preparation) in 1% Tween 80; n-hexyl ether derivative 40 in 1% Tween 80. After 1 or 5 days the mice were restrained without anesthesia in aluminum holders and one hind foot of each mouse was illuminated with light from a dye laser 171 (Spectra Physics). Illumination conditions (i.e., light dose, dose rate and wavelength) were as follows: Photofrin®, 5 mg/kg; BPD 5.0 mg/k (3.0 h), n-hexyl ether derivative 40 5.0 mg/kg (24 h) and 1.0 mg/kg (3 h). Light dose was measured with a Coherent 210 power meter and wavelength was measured with a PTR Optics monochromator. Sensitizer does for the foot response experiments corresponded to the lowest dose required to give maximum tumor control measured 7 days after treatment (see Table 3). Foot response was graded daily according to the scale in the legend to FIG. 13. Animals were euthanized immediately after peak foot scores were obtained.

In vivo Reflection Spectroscopy: The absorption spectrum of a compound in living tissue can be recorded using the instrument and technique which we have developed (Potter, W. R., Patent Disclosure, Roswell Park Cancer Institute, Buffalo, N.Y., August 1993). The experiment measures the light which scatters through the tissue. The light originates in a high pressure Xenon arc lamp and passes through a grating monochrometer to a 90 Hz chopper and then into a 400 micron diameter quartz fiber. The distal end of this fiber is placed in contact with the tissue (e.g. an experimental mouse tumor) and the light is collected by a second fiber placed in contact with the tissue at a fixed distance (3 to 5 mm) from the first fiber. The non invasive character of this measurement makes data collection possible at a number of time points after the i.v. injection of an experimental light absorbing compound (e.g. a potential photosensitizer). The light signal is detected by a photodiode. The photo current is converted into a voltage, amplified by a tuned (90 Hz) amplifier and synchronously detected. The chopping at 90 Hz and synchronous detection makes working in normal lighting possible.

Experimental technique: The mouse is first anesthesized using either Pentobarbital or Ketamine Xylazine i.p. The optical power as a function of wavelength is recorded before the i.v. injection of the sensitizer. The monochrometer is set to the expected longest wavelength of the experimental drug's absorption spectrum. The drug is then administered by tail vein injection and the light signal recorded as a function of time. When light level is relatively stable (on a scale of min) the absorption spectrum is recorded for a second time. The second spectrum contains a component due to the presence of the drug in the tumor. This in vivo drug absorption spectrum is best displayed by taking the ratio of the post-injection spectrum to the pre-injection spectrum (see FIG. 14). This ratio offers the same advantages as a double beam absorption spectrophotometer. The pre-injection mouse data can be thought of as the reference beam sample (typically a cuvette and solvents) and the post-injection data as the sample beam containing everything in the reference beam plus the experimental drug. The ratio of these two spectra is of course not influenced by the wavelength dependence of the light signal which characterizes the instrument.

The ratio is the drug absorption spectrum in tissue. As a safeguard against day to day or hour to hour drift in the total light output of the lamp, both spectra (pre- and post-injection) are normalized by dividing by the signal strength at a wavelength (e.g. 800 nm) where the drug absorption is negligible. The uptake and clearance, together with binding or metabolic shifts in the absorption spectra of a sensitizer, can be followed non invasively in the same mouse over a period of hours or days post injection.

In vivo Biological Activity: The in vivo photosensitizing ability of all the sensitizers was compared with that of commercial BPD in DBA/2 mice bearing subcutaneously implanted SMT-F tumors, a method previously described by Dougherty et al. All photosensitizers, including commercial BPD (mixture of 21 and 22) were first dissolved in a minimum quantity of Tween 80 and then diluted with 0.9% saline, to a final concentration of 1% Tween 80.

It can be seen from Table 3 that commercial BPD was quite effective at a dose of 5.0 mg/kg, 3 h post i.v. injection (4 out of six mice were tumor free at day 30). However, at the same dose there was no tumor response when the mice were treated with light 24 h after injecting the drug. Reducing the dose to 1.0 mg/kg at 3 h post injection gave a slightly reduced tumor response at day 2, and by day 7 there was 100% tumor regrowth. In order to compare the in vivo activity of photosensitizers 20, 23, 27, 28, 31, 36, 37, 40, 41, 42 and 45 with commercial BPD, these sensitizers were initially injected at a dose of 1.0 mg/kg and the results are as follows: The dimethyl ester derivatives of cis- and trans-isomers of ring "A" as well as ring "B" Diels Alder adducts 20, 28, 36, 41 showed activity similar to BPD. The acetyl derivatives 23, 31, 37 and 42 were difficult to dissolve, and were found to be inactive at the same dose. However, replacement of the vinyl with a 1-hexyloxyethyl group induced a remarkable difference in photosensitizing activity. For example, photosensitizers 27 (cis- isomer, ring "A" modified) and 35 (cis-isomer, ring "B" modified) both showed good antitumor activity. At a similar dose, among the trans isomers, the 1-hexyloxyl derivative 40 (ring "A" modified) was found to be more active than the ring "B" modified isomer 45. Sensitizer 40 also gave excellent activity at a dose of 5.0 mg/kg, treated 24 h. post i.v. injection of the drug. Under similar conditions, commercial BPD did not show any tumorcidal activity whatsoever.

Figure 13:
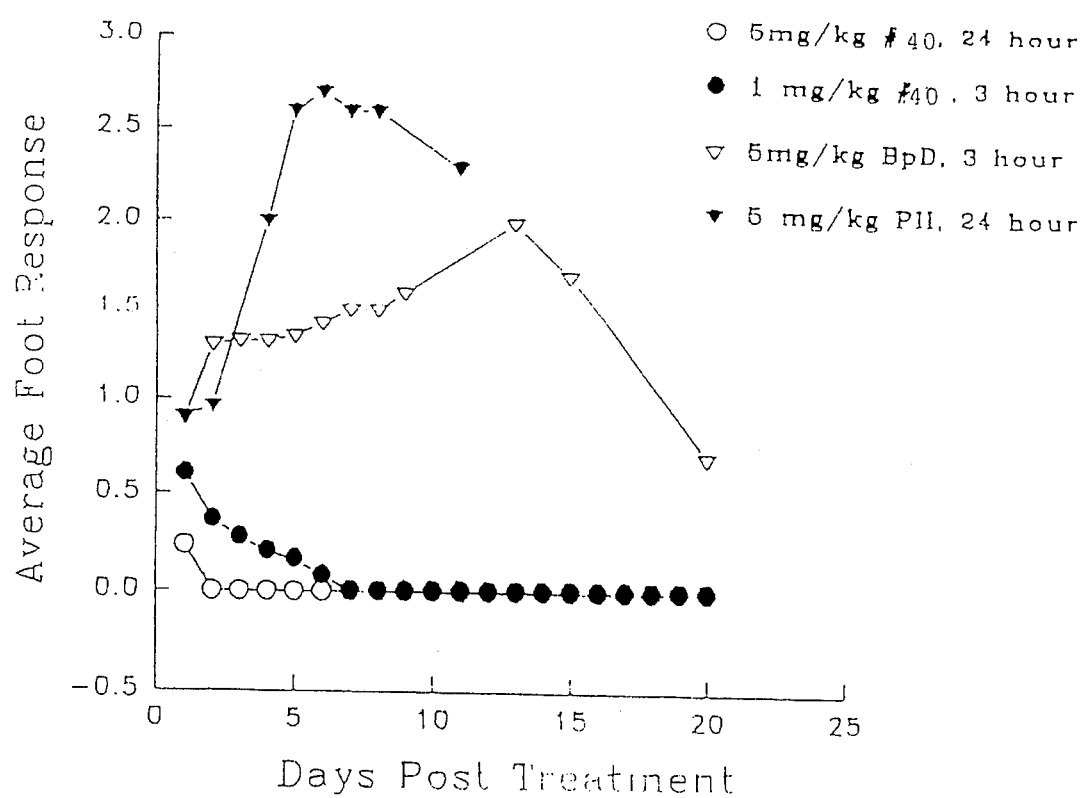
FIG. 13 is a graph illustrating foot response against days post treatment comparing compound 13 with BPD and Photofrin II®.

As can be seen from FIG. 13, photosensitizer 40 at a dose of 5.0 mg/kg (24 h post injection) or 1.0 mg/kg (3 h post injection) showed reduced skin phototoxicity when compared to Photofrin® (5.0 mg/kg, 24 h post injection), and BPD (5.0 mg/kg, 3 h post injection).

The results presented in the FIG. 14 show the in vivo absorption spectrum of 40 by measurement of the light diffusing through an SMT-F tumor in the skin of a DBA mouse. The data are taken with two optical fibers in contact with the tumor and separated by a distance of 5 mm. One of the fibers carries 90 Hz chopped light from a Xenon arc lamp and grating monochrometer to the tissue. The second fiber carries light from the tissue to a photodiode detector connected to a current to voltage converter and then to a lock-in amplifier tuned to 90 Hz. The animal is anesthetized and the fibers held motionless by a mechanical fixture. The animal was anesthetized for a second time to produce the 24 h data. The spectra are normalized to the long wavelength limit by dividing with the signal strength at a wavelength when the drug absorption is negligible. The result is thus compensated for small drift in light output from hour to hour or day to day. Each curve is the ratio of the normalized spectrum pre-injection to the normalized spectrum at various times post-injection. The spectra at 105 minutes and 24 h post-injection are shown.

From these results it can be seen that replacing the vinyl group with a n-hexyl ether side chain effects a significant improvement in photosensitizing efficacy. We believe that the presence of the hexyl ether side chain makes the molecule more hydrophobic which may help in localizing the drug in tumor. BPD, on the other hand, did not show any photosensitizing activity even at a dose of 5.0 mg/kg, treated 24 h post i.v. injection, which suggests that this drug has little retention in tumor or is metabolized to an inactive material. We also observed that cis and trans isomers of hexyl ether derivatives did not show much difference in their photosensitizing efficacy. Thus, the configuration of the molecule appears to make little difference in binding the molecules to tumor sites. However, from a synthetic point of view the cis- isomer has a minor advantage in that it was obtained in much better yield than the corresponding trans-isomer. From these results, we show that, as in the porphyrin (Evenson, J. F.; Sommer, S.; Rimington, C.; and Moan, J., [1987] "Photodynamic Therapy of CH3 Mouse Mammary Carcinoma with Hematoporphyrin Diethers as Sensitizers", *Br. J. Cancer* 55, pp. 483–486), chlorin and pheophorbide series (Pandey, R. K.; Bellnier, D. A.; Smith, K. M.; Dougherty, T. J., [1991] "Chlorin and Porphyrin Derivatives as Potential Photosensitizers in Photodynamic Therapy", *Photochem Photobiol* 53, pp 65–72), the hexyl ether derivatives of BPD also help in tumor localizing efficacy. A number of questions still remain unanswered regarding their binding site and mechanism of localization. Encouraged with these preliminary in vivo data, detailed biological studies with sensitizers 20, 23, 27, 28, 31, 36, 37, 40, 41, 42 and 45 (at different doses and time intervals) are in progress. In order to further explore the effect of various substituents upon biological activity, the synthesis of a variety of BPDs with a variable hydrophobic substituents are in progress (Pandey, R. K.; Meunier, I.; Dougherty, T. J.; Smith, K. M., "Alkyl Ether Analogues of Benzoporphyrin Derivatives as Improved Photosensitizers for PDT", Patent Disclosure, Roswell Park Cancer Institute, Buffalo, September 1993).

TABLE 1

Atomic coordinates [× 10⁴] for trans-36.

| | x | y | z |
|---|---|---|---|
| N(21) | 5204(4) | 7857(3) | 8810(3) |
| N(22) | 3379(4) | 8619(3) | 7367(3) |
| N(23) | 5747(4) | 8433(3) | 5689(3) |
| N(24) | 7556(4) | 7648(3) | 7075(3) |
| C(1) | 6190(5) | 7497(4) | 9315(4) |
| C(2) | 5648(5) | 7599(4) | 10420(4) |
| C(21) | 6027(5) | 6667(4) | 11312(3) |
| C(22) | 5039(5) | 6839(4) | 12313(3) |
| C(23) | 3756(5) | 7383(4) | 12344(4) |
| C(24) | 3241(5) | 7809(4) | 11424(4) |
| C(25) | 6132(7) | 5620(5) | 11138(5) |
| C(26) | 5160(9) | 4231(6) | 11439(8) |
| C(27) | 5523(5) | 6324(4) | 13253(4) |
| C(28) | 5260(6) | 6303(4) | 14983(4) |
| C(29) | 6058(5) | 8554(4) | 10499(4) |
| O(1) | 7147(5) | 5146(3) | 10662(4) |
| O(2) | 5053(5) | 5271(4) | 11529(5) |
| O(3) | 6542(5) | 5640(3) | 13278(3) |
| O(4) | 4750(4) | 6689(3) | 14064(3) |
| C(3) | 4130(5) | 7843(4) | 10516(4) |
| C(4) | 3973(4) | 8081(6) | 9463(3) |
| C(5) | 2723(5) | 8445(4) | 9224(4) |
| C(6) | 2435(5) | 8682(4) | 8279(3) |
| C(7) | 1129(5) | 9057(4) | 8069(4) |
| C(71) | −182(5) | 9249(4) | 8854(4) |
| C(8) | 1317(5) | 9224(4) | 7023(3) |
| C(81) | 302(5) | 9634(4) | 6421(4) |
| C(82) | −924(6) | 10156(6) | 6670(5) |
| C(9) | 2741(5) | 8949(3) | 6581(3) |
| C(10) | 3403(5) | 9042(4) | 5557(4) |
| C(11) | 4789(5) | 8823(3) | 5127(3) |
| C(12) | 5409(5) | 8969(4) | 4037(3) |
| C(121) | 4662(5) | 9411(4) | 3204(3) |
| C(13) | 6764(5) | 8643(4) | 3941(3) |
| C(131) | 7882(5) | 8576(4) | 2982(4) |
| C(132) | 8277(5) | 17501(5) | 2792(4) |
| C(133) | 9432(6) | 7378(5) | 1881(1) |
| C(134) | 10847(7) | 6218(6) | 883(5) |
| O(5) | 10053(4) | 3034(3) | 1361(3 |
| O(6) | 9719(4) | 6429(3) | 1722(3) |
| C(14) | 6956(5) | 8325(4) | 4980(3) |
| C(15) | 8230(5) | 7964(4) | 5195(4) |
| C(16) | 8502(5) | 7649(4) | 6149(4) |
| C(17) | 9813(5) | 7219(4) | 6380(4) |
| C(171) | 11131(5) | 7079(5) | 5587(4) |
| C(172) | 11587(7) | 6032(6) | 5345(5) |
| C(173) | 11398(6) | 6008(6) | 4365(5) |
| C(174) | 11860(10) | 4917(6) | 3305(6) |
| O(7) | 10937(5) | 6734(4) | 3741(3) |
| O(8) | 11847(5) | 5031(4) | 4252(4) |
| C(18) | 9620(5) | 6959(4) | 7423(4) |
| C(181) | 10691(5) | 6460(5) | 8015(4) |
| C(19) | 8203(5) | 7230(4) | 7873(4) |
| C(20) | 7554(5) | 7181(4) | 8887(4) |

TABLE 2

Atomic coordinates [× 10⁴] for cis-20.

| | x | y | z |
|---|---|---|---|
| N(21) | −268(7) | 8385(4) | 9463(3) |
| N(22 | −2636(7) | 10091(4) | 10082(3) |
| N(23) | −3000(7) | 9153(4) | 11718(3) |
| N(24) | −625(6) | 7492(4) | 11152(3) |
| C(1) | 634(8) | 7522(5) | 9291(4) |
| C(2) | 1329(8) | 7435(4) | 8337(4) |
| C(21) | 3133(8) | 7050(5) | 8152(4) |
| C(22) | 3772(8) | 7419(5) | 7288(4) |
| C(23) | 3016(8) | 8239(5) | 6949(4) |
| C(24) | 1704(8) | 8854(5) | 7391(4) |
| C(25) | 3523(9) | 5934(5) | 8218(5) |
| C(26) | 3825(12) | 4432(6) | 7584(6) |
| C(27) | 5321(8) | 6934(5) | 6937(4) |
| C(28) | 7302(10) | 6795(6) | 5785(5) |
| C(29) | 256(9) | 6868(5) | 7865(4) |
| O(1) | 3923(6) | 5523(3) | 8868(3) |
| O(2) | 3363(6) | 5477(3) | 7517(3) |
| O(3) | 6263(6) | 6402(4) | 7348(3) |
| O(4) | 5701(6) | 7164(3) | 6120(3) |
| C(3) | 968(8) | 8499(5) | 8089(4) |
| C(4) | −150(8) | 8988(5) | 8765(4) |
| C(5) | −1013(9) | 9917(5) | 8692(4) |
| C(6) | −2166(8) | 10427(5) | 9281(4) |
| C(7) | −3219(8) | 11307(5) | 9138(4) |
| C(71) | −3171(9) | 11872(5) | 8305(4) |
| C(8) | −4293(8) | 11498(5) | 9840(4) |
| C(81) | −5642(8) | 12278(5) | 9953(5) |
| C(82) | −5658(13) | 13221(7) | 9694(6) |
| C(9) | −3903(8) | 10734(5) | 10441(4) |
| C(10) | −4651(9) | 10624(5) | 11266(4) |
| C(11) | −4206(8) | 9900(5) | 11859(4) |
| C(12) | −4979(9) | 9890(5) | 12736(5) |
| C(121) | −6410(9) | 10582(5) | 13088(4) |
| C(13) | −4103(9) | 9145(5) | 13123(4) |
| C(131) | −4310(8) | 8808(5) | 14036(4) |
| C(132) | −5566(9) | 8140(6) | 14212(5) |
| C(133) | −7190(9) | 8682(5) | 14483(4) |
| C(134) | −9901(17) | 8890(13) | 14282(13) |
| O(5) | −8291(9) | 8385(7) | 14058(7) |
| O(6) | −7457(6) | 9343(4) | 14987(3) |
| C(14) | −2911(8) | 8658(5) | 12475(4) |
| C(15) | −1885(9) | 7809(5) | 12608(4) |
| C(16) | −864(8) | 7239(5) | 11999(4) |
| C(17) | 73(9) | 6308(5) | 12108(4) |
| C(171) | 283(9) | 5801(5) | 12955(4) |
| C(172) | 1749(9) | 6055(6) | 13366(4) |
| C(173) | 1596(10) | 5989(6) | 14316(5) |
| C(174) | 2960(11) | 5695(7) | 15571(4) |
| O(7) | 355(8) | 6141(6) | 14757(3) |
| O(8) | 2988(6) | 5746(4) | 14636(3) |
| C(18) | 842(9) | 6000(5) | 11324(5) |
| C(181) | 1922(8) | 5080(5) | 11095(4) |
| C(19) | 367(8) | 6756(5) | 10723(4) |
| C(20) | 920(8) | 6761(5) | 9858(4) |

TABLE 3

Comparative in vivo Antitumor Activity of Selected Photosensitizers#

| Compound | Dose (mg/kg) | Absorbance (max) | Time (h) between injection and light treatment | Tumor response (d)* 1–2 | 7 | 30 |
|---|---|---|---|---|---|---|
| BPD | 5.0 | 680 | 24 | 0 | — | — |
| (mix of | 5.0 | 680 | 3 | 6/6 | 6/6 | 4/6 |
| 21 & 22) | 1.0 | 680 | 3 | 2/6 | 0 | — |
| 27 | 1.0 | 676 | 3 | 6/6 | 4/6 | 1/6 |
| 35 | 1.0 | 676 | 3 | 6/6 | 6/6 | 2/6 |
| 40 | 1.0 | 676 | 3 | 6/6 | 3/6 | 3/6 |
|  | 5.0 | 676 | 24 | 6/6 | 6/6 | 5/6 |
| 45 | 1.0 | 676 | 3 | 6/6 | 4/6 | 0/6 |
|  | 5.0 | 676 | 24 | 6/6 | 6/6 | 0/6 |

4–6 mm diameter tumore were exposed to 75 mW/cm² for 30 min to deliver J/cm² from a tunable dye laser tuned to the maximum red absorption peak
*Non-palpable tumor

What is claimed is:

1. The compound having the formula:

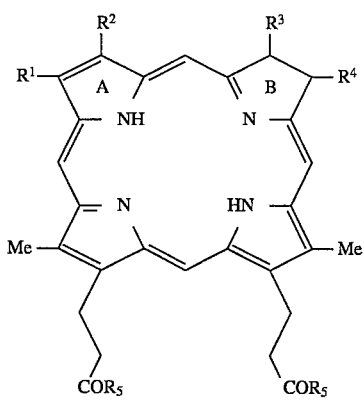

having R groups $R^1$, $R^2$, $R^3$, and $R^4$, wherein $R^1$ and $R^2$ are methyl or —CH(O—(CH$_2$)$_n$CH$_3$)CH$_3$ or are joined together to form the group D and wherein $R^3$ and $R^4$ are methyl or —CH(O—(CH$_2$)$_n$CH$_3$)CH$_3$ or are joined together to form the group D; provided that one of $R^1$ and $R^2$ or $R^3$ and $R^3$ are joined together to form the group D wherein one of the remaining R groups is methyl and one of the remaining R groups is —CH(O—(CH$_2$)$_n$CH$_3$)CH$_3$, where n is an integer of 5 through 7 and group D is:

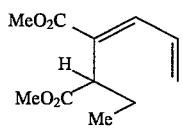

and $R_5$ is independently at each occurrence —OR$_6$ where $R_6$ is lower alkyl of 1 through 7 carbon atoms or $R_6$ is an amino acid residue.

2. The compound having the formula:

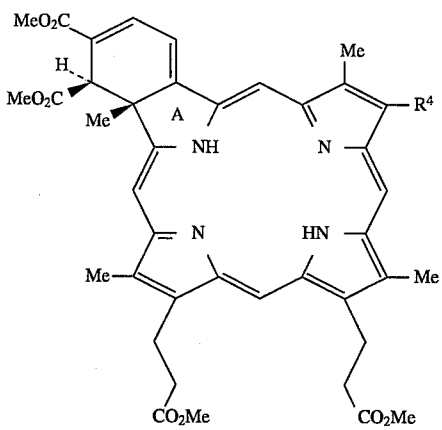

wherein $R^4$ is —CH(O—(CH$_2$)$_5$CH$_3$)CH$_3$.

3. The compound having the formula:

25
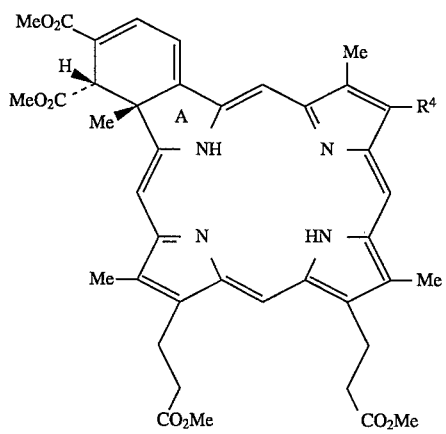
wherein R⁴ is —CH(O—(CH₂)₅CH₃)CH₃.
4. The compound having the formula:
26
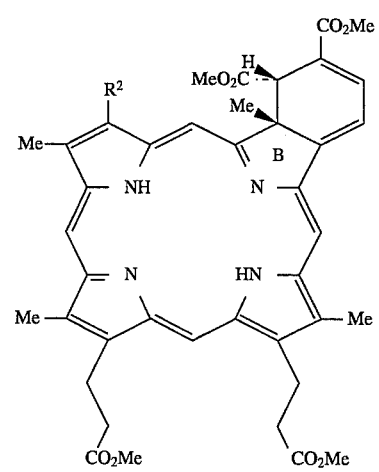
wherein R² is —CH(O—(CH₂)₅CH₃)CH₃.
* * * * *